US008467872B2

(12) United States Patent
Hareland

(10) Patent No.: US 8,467,872 B2
(45) Date of Patent: Jun. 18, 2013

(54) FAULT-TOLERANT HIGH VOLTAGE DELIVERY IN AN IMPLANTABLE MEDICAL DEVICE

(75) Inventor: Scott A. Hareland, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/221,558

(22) Filed: Aug. 30, 2011

(65) Prior Publication Data

US 2013/0053910 A1    Feb. 28, 2013

(51) Int. Cl.
*A61N 1/00* (2006.01)

(52) U.S. Cl.
USPC .............................. 607/27; 607/62

(58) Field of Classification Search
USPC ........................ 607/27–29, 59, 62–64, 9, 4–8
See application file for complete search history.

(56) References Cited

U.S. PATENT DOCUMENTS

| 4,800,883 | A |   | 1/1989  | Winstrom        |       |
|-----------|---|---|---------|-----------------|-------|
| 4,830,006 | A |   | 5/1989  | Haluska et al.  |       |
| 4,953,551 | A |   | 9/1990  | Mehra et al.    |       |
| 5,344,430 | A | * | 9/1994  | Berg et al.     | 607/8 |
| 5,873,893 | A |   | 2/1999  | Sullivan et al. |       |
| 6,493,586 | B1|   | 12/2002 | Stahmann et al. |       |
| 7,764,998 | B1|   | 7/2010  | Raddatz         |       |
| 2008/0300660 | A1 | * | 12/2008 | John    | 607/61 |
| 2008/0306561 | A1 | * | 12/2008 | Sweeney | 607/5  |
| 2010/0228307 | A1 |   | 9/2010  | Kroll et al. |   |

OTHER PUBLICATIONS

Non-Final Office Action from U.S. Appl. No. 13/221,617, dated Nov. 23, 2012, 10 pp.
Amendment from co-pending U.S. Appl. No. 13/221,617, filed Feb. 25, 2013 (11 pages).
U.S. Appl. No. 13/221,617, by Scott A. Hareland, filed Aug. 30, 2011.

* cited by examiner

*Primary Examiner* — Scott Getzow
(74) *Attorney, Agent, or Firm* — Michael C. Soldner

(57) ABSTRACT

A medical device includes an energy storage device, a plurality of electrodes, a memory, a switching circuit, and a processing module. The energy storage device stores electrical energy for delivery of defibrillation therapy to a heart. The memory stores N therapy configurations, each of the N therapy configurations defining which of the plurality of electrodes are used to deliver defibrillation therapy and further defining a waveform to be applied during delivery of defibrillation therapy. The switching circuit is configured to connect the plurality of electrodes to the energy storage device. The processing module is configured to control the switching circuit to deliver defibrillation therapy according to a first therapy configuration, detect a fault during delivery of the defibrillation therapy according to the first therapy configuration, and select a second therapy configuration based on when the fault was detected during delivery of the defibrillation therapy according to the first therapy configuration.

28 Claims, 20 Drawing Sheets

Potential Delivery Path Impedance Bottlenecks

| Vector (b=bi, m=mono) | $PW_{1MAX}$ timeout, $PW2<PW_{2MAX}$, Possible Ω issue in: | $PW1<PW_{1MAX}$, $PW_{2MAX}$ timeout, Possible Ω issue in: | $PW_{1MAX}$ and $PW_{2MAX}$ timeout |
|---|---|---|---|
| AX>B (b) | $(A_H \& X_H)$ or $B_L$ | $(A_L \& X_L)$ or $B_H$ | $S_1$ or HV lead RVC or (CAN & HV lead SVC) |
| B>AX (b) | $(A_L \& X_L)$ or $B_H$ | $(A_H \& X_H)$ or $B_L$ | $S_1$ or HV lead RVC or (CAN & HV lead SVC) |
| A>B (b) | $A_H$ or $B_L$ | $A_L$ or $B_H$ | $S_1$ or HV lead RVC or CAN |
| B>A (b) | $B_H$ or $A_L$ | $A_H$ or $B_L$ | $S_1$ or HV lead RVC or CAN |
| B>X (b) | $B_H$ or $X_L$ | $X_H$ or $B_L$ | $S_1$ or HV lead RVC or HV lead SVC |
| X>B (b) | $X_H$ or $B_L$ | $B_H$ or $X_L$ | $S_1$ or HV lead RVC or HV lead SVC |
| AX>B (m) | $(A_H \& X_H)$ or $B_L$ | --- | $S_1$ or HV lead RVC or (CAN & HV lead SVC) |
| B>AX (m) | $(A_L \& X_L)$ or $B_H$ | --- | $S_1$ or HV lead RVC or (CAN & HV lead SVC) |
| A>B (m) | $A_H$ or $B_L$ | --- | $S_1$ or HV lead RVC or CAN |
| B>A (m) | $B_H$ or $A_L$ | --- | $S_1$ or HV lead RVC or CAN |
| B>X (m) | $B_H$ or $X_L$ | --- | $S_1$ or HV lead RVC or HV lead SVC |
| X>B (m) | $X_H$ or $B_L$ | --- | $S_1$ or HV lead RVC or HV lead SVC |
| others | config. dependent | config. dependent | config. dependent |

FIG. 19

Reconfiguration Options for Faulty HV delivery signatures

| Suspected faulty switch(es) | Based upon failure signature | Potential reconfiguration safety vectors |
|---|---|---|
| $A_H$ & $X_H$ | AX>B (b or m) $PW_1$<br>B>AX (b) $PW_2$ | B>AX (m)[1] |
| $A_H$ | A>B (b or m) $PW_1$<br>B>A (b) $PW_2$ | B>A (m)[1]<br>B>X (b)[2]<br>X>B (b)[3] |
| $X_H$ | X>B (b or m) $PW_1$<br>B>X (b) $PW_2$ | B>A (b)[2]<br>B>AX (m)[1]<br>B>A (m)[1]<br>A>B (m)[3] |
| $B_H$ | AX>B (b) $PW_2$<br>B>AX (b or m) $PW_1$<br>A>B (b) $PW_2$<br>B>A (b or m) $PW_1$<br>X>B (b) $PW_2$<br>B>X (m) $PW_1$ | AX>B (m)[1]<br>A>B (m)[1]<br>X>B (m)[1] |
| $A_L$ & $X_L$ | AX>B (b) $PW_2$<br>B>AX (b) $PW_1$ | AX>B (m)[1] |
| $A_L$ | B>A (b) $PW_2$<br>A>B (b or m) $PW_1$ | A>B (m)[1]<br>B>X (b or m)[1,2]<br>X>B (b or m)[1,2] |
| $X_L$ | B>X (b or m) $PW_2$<br>X>B (b) $PW_1$ | A>B (b or m)[1,2]<br>B>A (b or m)[1,3]<br>X>B (m)[2] |
| $B_L$ | AX>B (b or m) $PW_1$<br>B>AX (b) $PW_2$<br>A>B (b or m) $PW_1$<br>B>A (b) $PW_2$<br>X>B (b or m) $PW_1$<br>B>X (b) $PW_2$ | B>AX (m)[1]<br>B>A (m)[1] |

FIG. 20

FAULT-TOLERANT HIGH VOLTAGE DELIVERY IN AN IMPLANTABLE MEDICAL DEVICE

TECHNICAL FIELD

The disclosure relates to techniques for providing fault tolerance in an implantable medical device, and more particularly, to techniques for providing tolerance to high impedance faults in an implantable medical device.

BACKGROUND

Implantable medical devices (IMDs), such as implantable cardioverter-defibrillators, may detect a cardiac arrhythmia and provide various electrical therapies in response to detection of the arrhythmia. Therapies provided by an IMD in response to a detected arrhythmia may include anti-tachycardia pacing (ATP) therapy, cardioversion therapy, and/or defibrillation therapy, depending on the type of arrhythmia detected.

Some detected arrhythmias may be life-threatening. Ventricular tachycardia (VT) and ventricular fibrillation (VF) may be considered to be life-threatening arrhythmias. In examples where an IMD detects such a life-threatening arrhythmia, the IMD may provide a defibrillation shock to the patient's heart in order to terminate the arrhythmia and return the patient's heart rhythm back to a normal rhythm.

An IMD may include components that are dedicated to producing a defibrillation shock in response to detection of a life-threatening arrhythmia. For example, an IMD may include high-voltage capacitors for storing electrical charge for subsequent delivery during a defibrillation shock. Additionally, the IMD may include a delivery circuit that transfers the electrical charge from the high-voltage capacitors to the heart. During operation, an IMD may typically monitor a patient's heart rate, or other parameters (e.g., morphology, onset, etc.) in order to detect an arrhythmia. If the IMD detects a life-threatening arrhythmia, the IMD may charge the high-voltage capacitors and control the delivery circuit to transfer the energy from the high-voltage capacitors to the patient's heart using either a biphasic or a monophasic waveform. Delivery of the defibrillation shock may terminate the detected arrhythmia and return the heart to a normal rhythm.

SUMMARY

An IMD according to the present disclosure (e.g., an implantable cardioverter-defibrillator) may detect cardiac arrhythmias and apply high-energy therapy (e.g., cardioversion and/or defibrillation) to the heart in order to correct the detected arrhythmia. The IMD may deliver high-energy therapy according to a therapy configuration that specifies an electrode vector to be used during delivery of the therapy and that specifies the type of waveform (e.g., biphasic/monophasic/multiphasic) to be used during delivery of the therapy. The IMD may include an energy storage device (e.g., high-voltage capacitors) that delivers the high-energy therapy through an electrical pathway to the patient's heart according to a specified therapy configuration. In some examples, the electrical pathway may include electrical switches, electrical interconnects, high-voltage leads, and electrodes.

Typically, the electrical pathway presents a low impedance path (e.g., a short circuit) from the energy storage device to the electrodes. However, in some examples, the electrical pathway may include faults that increase the impedance of the pathway as seen by the energy storage device. Such faults may be referred to herein as "high impedance faults." High impedance faults may occur in at least one of the electrical switches, electrical interconnects, leads, and electrodes of the IMD.

The IMD of the present disclosure may detect high impedance faults in the electrical pathway during delivery of the high-energy therapy according to a current therapy configuration. If the IMD detects a high impedance fault while delivering therapy according to a currently selected therapy configuration, the IMD may select a subsequent therapy configuration. The IMD may select the subsequent therapy configuration based on the electrode vector used while the fault was detected, the waveform used while the fault was detected, and based on when the fault occurred during the waveform (e.g., during a first or second phase of the biphasic waveform).

The IMD may use the subsequent therapy configuration to treat subsequently detected arrhythmias. If any future high impedance faults are detected during delivery of high-energy therapy according to the subsequently selected therapy configuration, the IMD may select a newer therapy configuration. The IMD may select the newer therapy configuration in a similar manner described above, e.g., based on the electrode vector used while the fault was detected, based on the waveform used while the fault was detected, based on when the fault occurred, and in some examples, based on prior knowledge of other failed therapy attempts.

The IMD of the present disclosure may continue to update therapy configurations in response to additional detections of high impedance faults during delivery of high-energy therapy. In this manner, the IMD of the present disclosure may step through a variety of different therapy configurations in order to bypass one or more detected high impedance faults. Stepping through a variety of different therapy configurations based on which therapy configurations include high impedance faults and based on when those high impedance faults occur may provide for robust delivery of high-energy therapy from the IMD in the event of a fault in a conductive pathway of the IMD that is presented as a high impedance fault.

In one example according to the present disclosure, a medical device comprises an energy storage device, a plurality of electrodes, a memory, a switching circuit, and a processing module. The energy storage device is configured to store electrical energy for delivery of defibrillation therapy to a heart. The memory stores N therapy configurations, each of the N therapy configurations defining which of the plurality of electrodes are used to deliver defibrillation therapy and further defining a waveform to be applied during delivery of defibrillation therapy. N is an integer that is greater than 1. The switching circuit is configured to connect the plurality of electrodes to the energy storage device. The processing module is configured to control the switching circuit to deliver defibrillation therapy according to a first therapy configuration of the N therapy configurations, detect a fault during delivery of the defibrillation therapy according to the first therapy configuration, and select a second therapy configuration of the N therapy configurations based on when the fault was detected during delivery of the defibrillation therapy according to the first therapy configuration.

In another example according to the present disclosure, a medical device comprises an energy storage device, a plurality of electrodes, a switching circuit, and a processing module. The energy storage device is configured to store electrical energy for delivery of defibrillation therapy to a heart. The switching circuit is configured to connect the plurality of electrodes to the energy storage device. The processing module is configured to control the switching circuit to deliver defibrillation therapy using a first set of the plurality of electrodes and using a biphasic waveform that includes first and second phases. The processing module is further configured to detect a fault during one of the first and second phases of the biphasic waveform and select a second set of the plurality of electrodes and one of a biphasic or monophasic waveform for delivery of a subsequent defibrillation therapy. The selection is based on which one of the first and second phases of the biphasic waveform included the detected fault.

In another example according to the present disclosure, a method comprises storing N therapy configurations in a memory of a medical device, each of the N therapy configurations defining which of a plurality of electrodes are used to deliver defibrillation therapy and further defining a waveform to be applied during delivery of defibrillation therapy. N is an integer that is greater than 1. The method further comprises controlling a switching circuit to deliver defibrillation therapy from an energy storage device according to a first therapy configuration of the N therapy configurations, detecting a fault during delivery of the defibrillation therapy according to the first therapy configuration, and selecting a second therapy configuration of the N therapy configurations based on when the fault was detected during delivery of the defibrillation therapy according to the first therapy configuration. The fault includes one of a high impedance fault and a short circuit fault. The high impedance fault is presented as a high impedance in a conductive path used during defibrillation therapy. The short circuit fault shunts current away from the heart during delivery of defibrillation therapy.

The details of one or more examples are set forth in the accompanying drawings and the description below. Other features, objects, and advantages will be apparent from the description and drawings, and from the claims.

BRIEF DESCRIPTION OF THE DRAWINGS

FIG. 19 is a table that shows potential delivery path impedance bottlenecks.

FIG. 20 is a table that lists potential reconfiguration options for faulty components.

DETAILED DESCRIPTION

Figure 1:
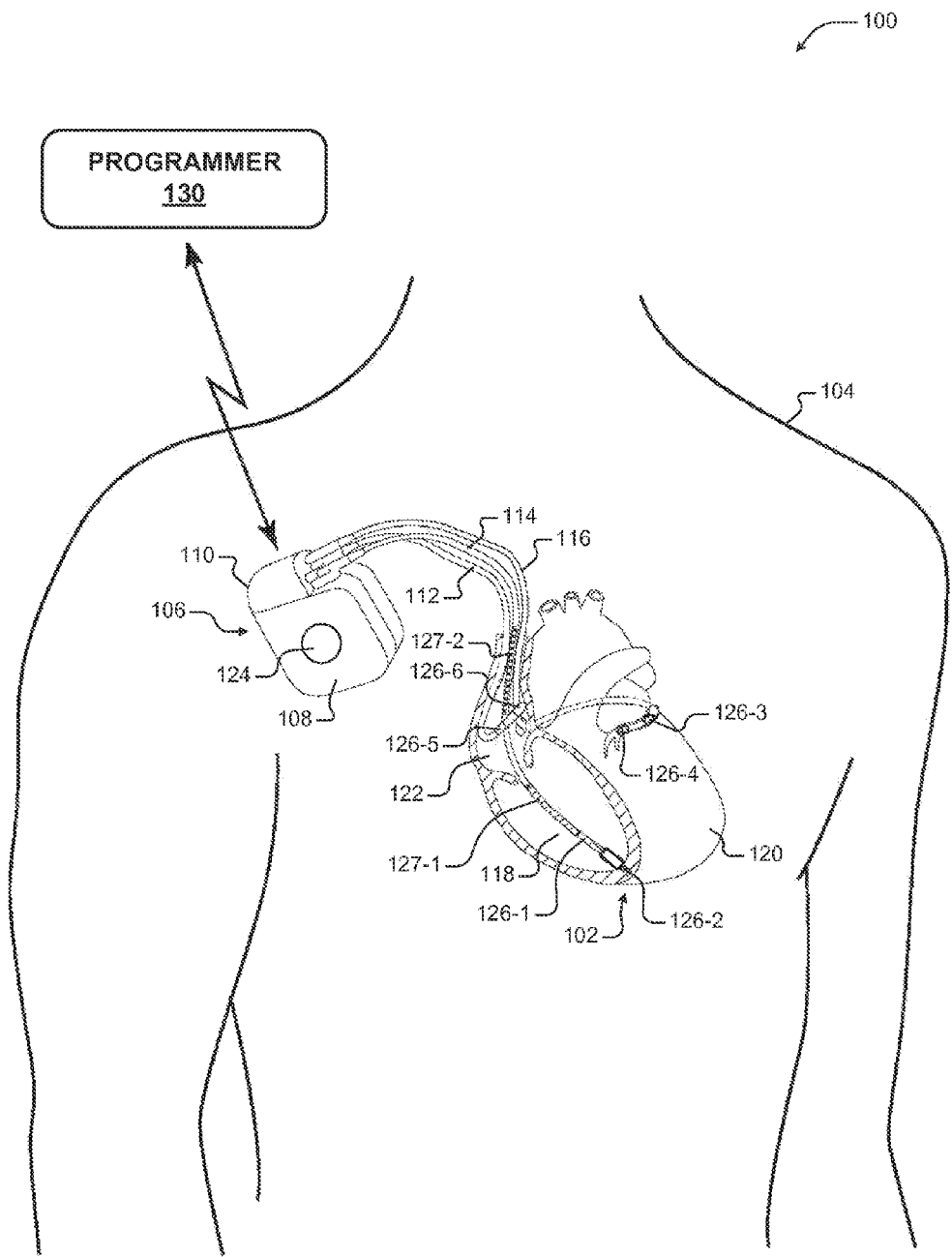
FIG. 1 shows an example system including an implantable medical device (IMD) that may be used to diagnose conditions of and provide therapy to a heart of a patient.

An IMD according to the present disclosure may detect an arrhythmia (e.g., VT/VF) and deliver therapy to terminate the arrhythmia. In some examples, the IMD may deliver defibrillation therapy in response to detection of potentially life-threatening arrhythmias, such as VT/VF. In other examples, the IMD may deliver cardioversion therapy in response to the detection of potentially life-threatening arrhythmias. High-energy electrical therapies, such as defibrillation therapy and cardioversion therapy, delivered by the IMD in response to detection of potentially life threatening arrhythmias may be referred to hereinafter as "high-energy therapies." Arrhythmias that may be typically treated by such high-energy therapies, such as VT/VF, may be referred to hereinafter as "shockable arrhythmias."

The IMD of the present disclosure may include an energy storage device (e.g., high-voltage capacitors) that may be used to store charge for delivery of high-energy therapy. The IMD may monitor the heart rhythm of the patient and, in response to detection of a shockable arrhythmia, store charge on the energy storage device and subsequently deliver the high-energy therapy to the patient using the stored charge. The IMD may deliver the high-energy therapy using a variety of electrical waveforms and electrode combinations. For example, the IMD may deliver the high-energy therapy using either a monophasic or a biphasic waveform. Although high-energy therapy is described herein as being delivered using either a monophasic or biphasic waveform, it is contemplated that high-energy therapy may be delivered using other waveforms, such a multiphasic waveforms.

The IMD may deliver the high-energy therapy to the heart using a plurality of different electrode combinations. In some examples, the IMD may deliver high-energy therapy using three electrodes, while in other examples, the IMD may deliver high-energy therapy using two electrodes. The combination of electrodes used to deliver the high-energy therapy may referred to hereinafter as an "electrode vector." As described herein, high-energy therapy may be delivered using the following electrodes: 1) electrode HVA, which is an electrode on the housing (i.e., can) of the IMD, 2) electrode HVB, which may be a defibrillation coil electrode in the right ventricle, and 3) electrode HVX, which may be a defibrillation coil electrode in the superior vena cava. An electrode vector may include any combination of the electrodes HVA, HVB, and HVX. Although electrodes HVA, HVB, and HVX are described herein as delivering high-energy therapy, it is contemplated that the IMD may deliver therapy using other electrodes. For example, the IMD may deliver therapy using a greater number of electrodes, or in some cases, other types of electrodes, such as patch electrodes.

Electrode vectors may be described using a notation that includes the greater-than symbol ">" to indicate the direction of current between electrodes during delivery of high-energy therapy. In one example, electrode vector "AX>B" may indicate that the direction of current is from the HVA electrode and HVX electrode to the HVB electrode. Example electrode vectors described herein that include three electrodes are electrode vectors "AX>B" and "B>AX." Electrode vectors described herein that include only two electrodes are electrode vectors "A>B", "B>A", "X>B", and "B>X." In some examples, electrode vectors may also include "A>X" and "X>A." While vectors "A>X" and "X>A" may not be conventionally used vectors, in some examples, "A>X" and "X>A" may provide a valid path, e.g., in the case where an epicardial patch electrode is connected as "X."

The IMD may include a memory that stores various high-energy therapy configurations. Each high-energy therapy configuration may specify an electrode vector and an electrical waveform to be delivered by the electrode vector. High-energy therapy configurations may be referred to hereinafter as "therapy configurations." One example therapy configuration may specify that high-energy therapy is to be delivered via electrode vector AX>B using a biphasic waveform. In other examples, therapy configurations may specify that high-energy therapy is to be delivered via electrode vector AX>B using a monophasic waveform, via electrode vector B>AX using a monophasic waveform, or via electrode vector B>AX using a biphasic waveform. In other examples, therapy configurations may specify that high-energy therapy is to be delivered via electrode vector A>B using a biphasic waveform, via electrode vector A>B using a monophasic waveform, via electrode vector B>A using a biphasic waveform, or via electrode vector B>A using a monophasic waveform. In still other examples, therapy configurations may specify that high-energy therapy is to be delivered via electrode vector X>B using a biphasic waveform, via electrode vector X>B using a monophasic waveform, via electrode vector B>X using a biphasic waveform, or via electrode vector B>X using a monophasic waveform. In some examples, the therapy configurations may also specify an amount of energy to be delivered.

The IMD of the present disclosure includes a processing module that detects shockable arrhythmias, controls charging of the energy storage device in response to detection of a shockable arrhythmia, and controls delivery of high-energy therapy according to a selected therapy configuration. The IMD may include a switching circuit that may be controlled in order to deliver the high-energy therapy according to the selected therapy configuration. Under control of the processing module, the switching circuit may connect the energy storage device to the electrode vector such that the waveform of the selected therapy configuration is delivered to the patient via the electrode vector of the selected therapy configuration.

The IMD of the present disclosure may detect a potential fault during delivery of the high-energy therapy. For example, the IMD may detect a high impedance fault during delivery of the high-energy therapy. A high impedance fault may generally describe a variety of different faults that may occur in the conductive pathway leading from the energy storage device to the electrodes during delivery of high-energy therapy. Typically, the conductive pathway leading from the energy storage device to the electrodes presents a low impedance pathway to the energy storage device, e.g., relative to the impedance of the patient between the electrodes. The presence of a high impedance fault in the conductive pathway from the energy storage device to the electrodes may tend to increase the impedance of the conductive pathway, e.g., such that the conductive pathway may not be approximated as a short circuit (i.e. very low impedance).

High impedance faults may include a variety of different faults within the IMD. A high impedance fault may occur in any component of the conductive pathway. The conductive pathway may include switches, interconnects, conductors in leads of the IMD, and electrodes at the end of the conductors. Each of these components may typically present a relatively low impedance (e.g., approximately a short circuit) when a high impedance fault is not present in these components. However, a high impedance fault in any of these components may cause the impedance of the components to deviate from a low impedance value to a higher impedance value, e.g., approaching that of an open circuit impedance. In some examples, switches that are responsible for connecting the energy storage device to the electrodes may malfunction and present a relatively high impedance, even when the switches are instructed to be in a closed state. In some examples, the interconnects between electrical components of the IMD may malfunction and present a high impedance instead of a short-circuit impedance. The interconnects may generally describe the conductive paths between electrical components, and may include the conductive traces, e.g., on a printed-circuit board. In some examples, conductors within the leads of the IMD may present a high impedance instead of a short-circuit impedance, e.g., when the conductors break (e.g., fracture) within the leads. In some examples, electrodes (e.g., coil electrodes) may also break (e.g., fracture) and present a high impedance instead of a short-circuit impedance.

An increase in the impedance of the conductive pathway, due to the presence of a high impedance fault, may tend to slow the rate at which energy is delivered to the heart during delivery of high-energy therapy. The processing module of the IMD may monitor the delivery of energy to the patient, and may detect a potential high impedance fault if energy is not delivered to the patient at a great enough rate, e.g., if a predetermined amount of energy is not delivered within a predetermined amount of time.

As described above, the IMD may deliver therapy according to a selected therapy configuration. Initially, the IMD delivers therapy according to a set of initial therapy configurations stored in memory. The initial therapy configurations may define a pattern of selection of therapy configurations used by the IMD when a high impedance fault has not been previously detected during delivery of therapy. Accordingly, the processing module may control delivery of high-energy therapy according to the initial therapy configurations in response to detection of arrhythmia, assuming a high impedance fault has not been detected during prior deliveries of high-energy therapy according to the initial therapy configurations.

The initial therapy configurations stored in memory may define a pattern of selection of therapy configurations that may be used by the IMD during attempts to treat a detected shockable arrhythmia. For example, the IMD may initially attempt to treat a shockable arrhythmia using a first one of the initial therapy configurations. If successful in treating the shockable arrhythmia, the IMD may return to monitoring heart rhythm. If unsuccessful in treating the shockable arrhythmia, the IMD may select a second one of the initial therapy configurations to treat the shockable arrhythmia. In this manner, the IMD may select consecutive therapy configurations from the initial therapy configurations in order to attempt to treat a shockable arrhythmia in different ways until a successful treatment is found.

The initial therapy configurations may be programmed into the device prior to implantation, e.g., as factory default settings, or programmed by a clinician. In other examples, the initial therapy configurations may be updated by a clinician, using a programmer, during the implantation procedure or after the device is implanted. The initial therapy configurations may define a variety of different electrode vector and waveform combinations, as well as different amounts of energies to be delivered during high-energy therapy. Typically, the initial therapy configurations, which may be programmed by a clinician, may not be programmed in a manner that selects a pattern of therapy configurations based on possible high impedance faults included in the IMD, but instead may be programmed by the clinician in order to provide efficacious therapy assuming that high impedance faults are not present in the IMD.

The IMD may deliver high-energy therapy according to the initial therapy configurations until a high impedance fault is detected during delivery of the high-energy therapy according to the initial therapy configurations. Upon detection of a high impedance fault during delivery of high-energy therapy according to the initial therapy configurations, the IMD may begin delivering high-energy therapy according to a set of high impedance therapy configurations stored in memory. The high impedance therapy configurations may define the selection of therapy configurations used by the IMD after a high impedance fault is detected during delivery of high-energy therapy. Accordingly, after detection of a high impedance fault, the processing module may control delivery of high-energy therapy according to the high impedance therapy configurations in response to detection of a shockable arrhythmia.

Each of the high impedance therapy configurations stored in memory may define an electrode vector (e.g., AX>B, A>X, etc.), a waveform (e.g., biphasic/monophasic), and transition data. The transition data may specify a subsequent therapy configuration to select in response to detection of a high impedance fault at the current therapy configuration selection. For example, if the processing module detects a high impedance fault while using a first therapy configuration, the processing module may determine a subsequent (i.e., second) therapy configuration to use by looking at the transition data that is associated with the current (i.e., first) therapy configuration. The processing module may then set the therapy configuration of the IMD to the second therapy configuration in order to attempt to bypass the potential fault. If a fault is then detected in the second therapy configuration, the processing module may set the therapy configuration to the therapy configuration indicated by the transition data of the second therapy configuration. In this manner, the IMD may determine a subsequent therapy configuration to use for the delivery of high-energy therapy based on the transition data of the current therapy configuration in which a high impedance fault is detected.

In addition to determining subsequent therapy configurations based on a current therapy configuration in which a high impedance fault is detected, the IMD may also determine the subsequent therapy selection based on when the high impedance fault was detected during the delivery of high-energy therapy. Accordingly, the IMD of the present disclosure may select a subsequent therapy configuration based on the current therapy configuration in which a fault is detected and based on when the detected fault occurred during delivery of high-energy therapy according to the current therapy configuration.

The transition data may specify the subsequent therapy configuration based on when the high impedance fault was detected during the current therapy configuration. For example, the transition data associated with a first therapy configuration may specify a second therapy configuration if a high impedance fault is detected during the first phase of the biphasic waveform of the first therapy configuration, and the transition data associated with the first therapy configuration may specify a third therapy configuration if a high impedance fault is detected during the second phase of the biphasic waveform of the first therapy configuration. In examples where the IMD may deliver a multiphasic waveform, transition data may specify a subsequent therapy based on which phase of the multiphasic waveform included a fault.

In summary, the IMD of the present disclosure may detect shockable arrhythmias and provide high-energy therapy according to a selected configuration therapy. If the IMD detects a high impedance fault during delivery of the high-energy therapy according to a currently selected therapy configuration, the IMD may select a subsequent therapy configuration based on the parameters of the current therapy configuration (e.g., the electrode vector and waveform) and based on when the high impedance fault occurred during delivery according to the current therapy configuration (e.g., during either the first or second phase of a biphasic waveform). In this manner, the IMD of the present disclosure may step through a variety of different therapy configurations in order to bypass one or more detected high impedance faults. Stepping through a variety of different therapy configurations based on which therapy configurations include high impedance faults and based on when those high impedance faults occur may provide for robust delivery of high-energy therapy from an IMD in the event that a high impedance fault is present in a conductive pathway of the IMD.

Figure 2:
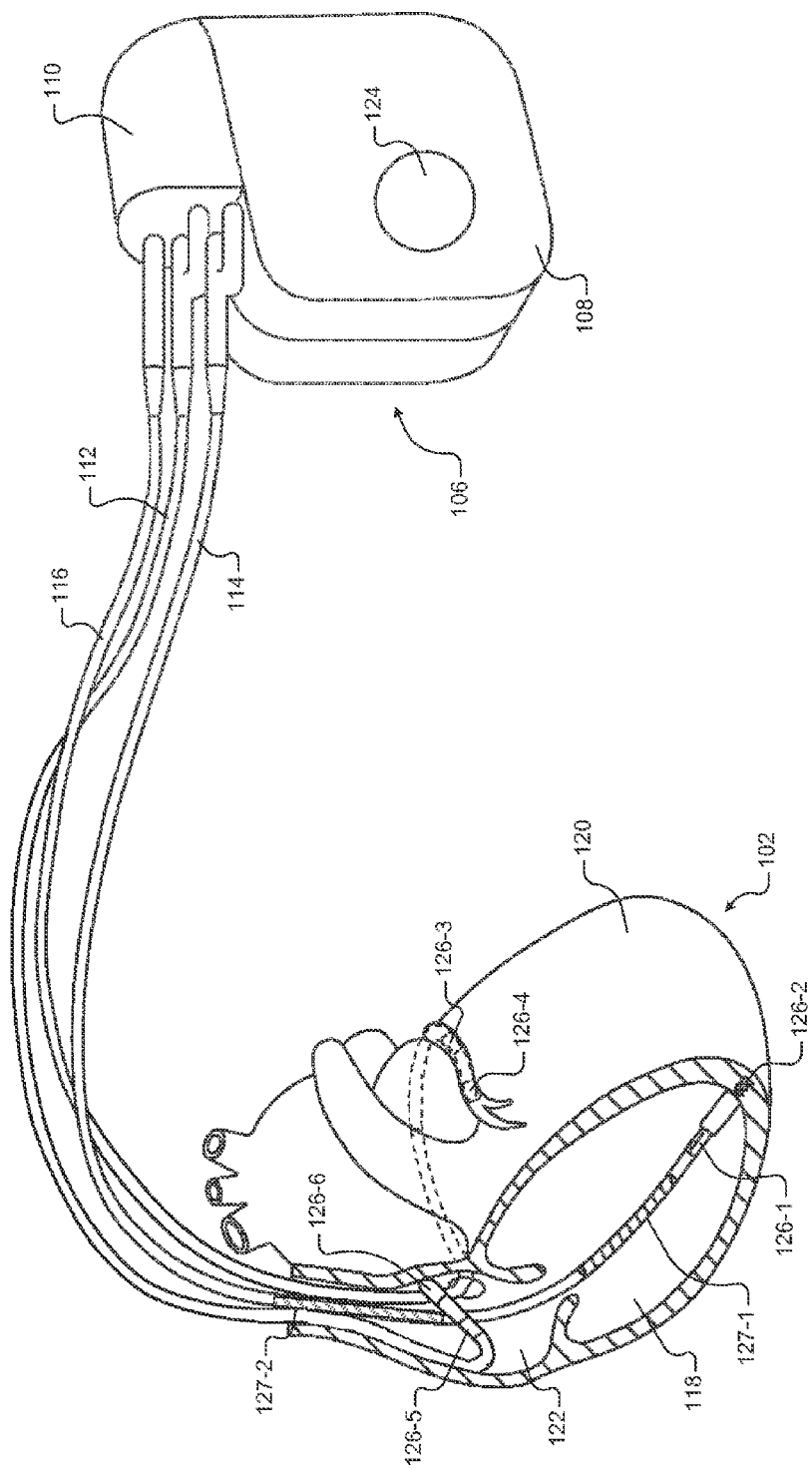
FIG. 2 shows a detailed view of the IMD of FIG. 1.
Figure 3:
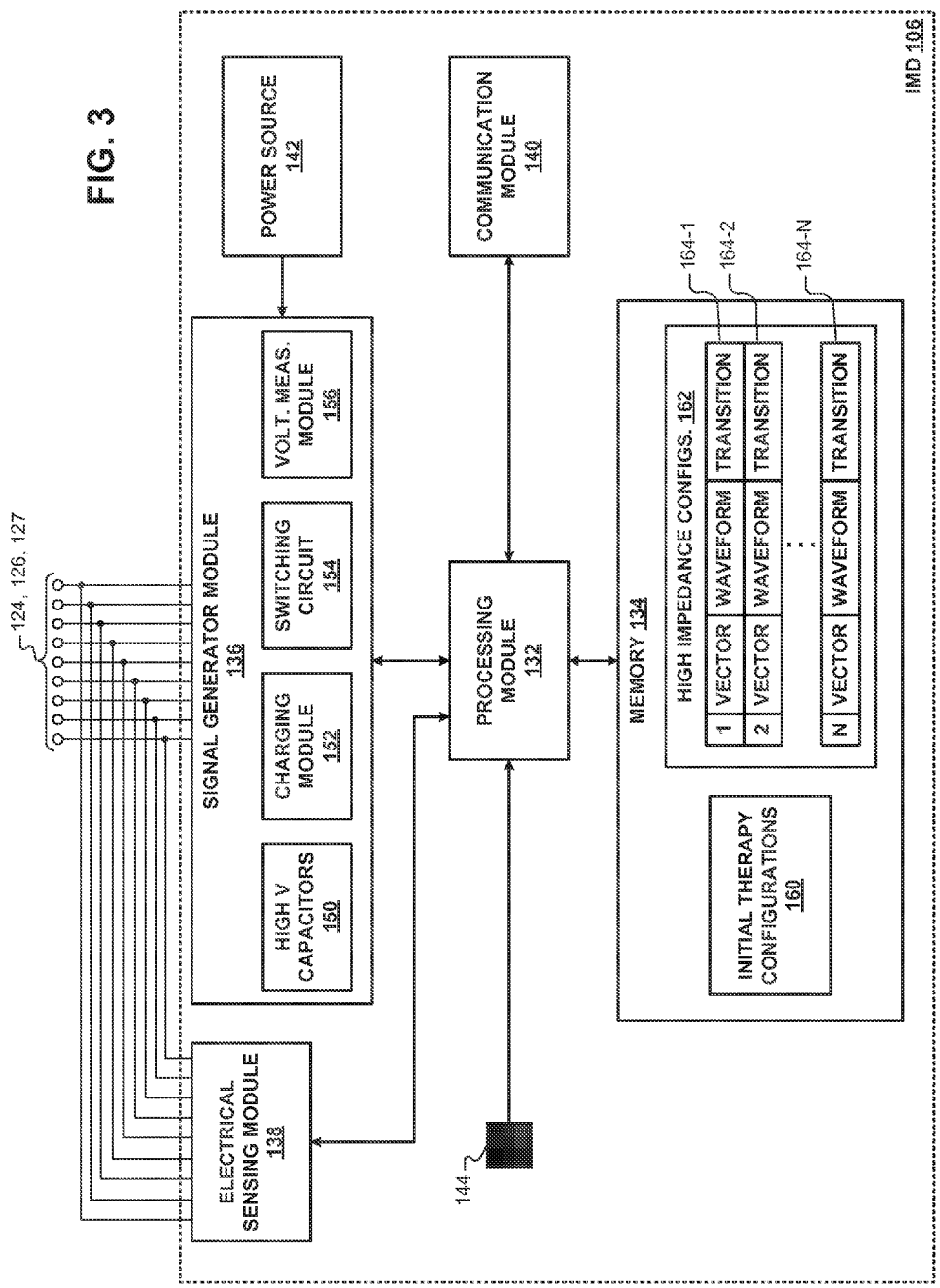
FIG. 3 shows a functional block diagram of an example IMD.
Figure 4:
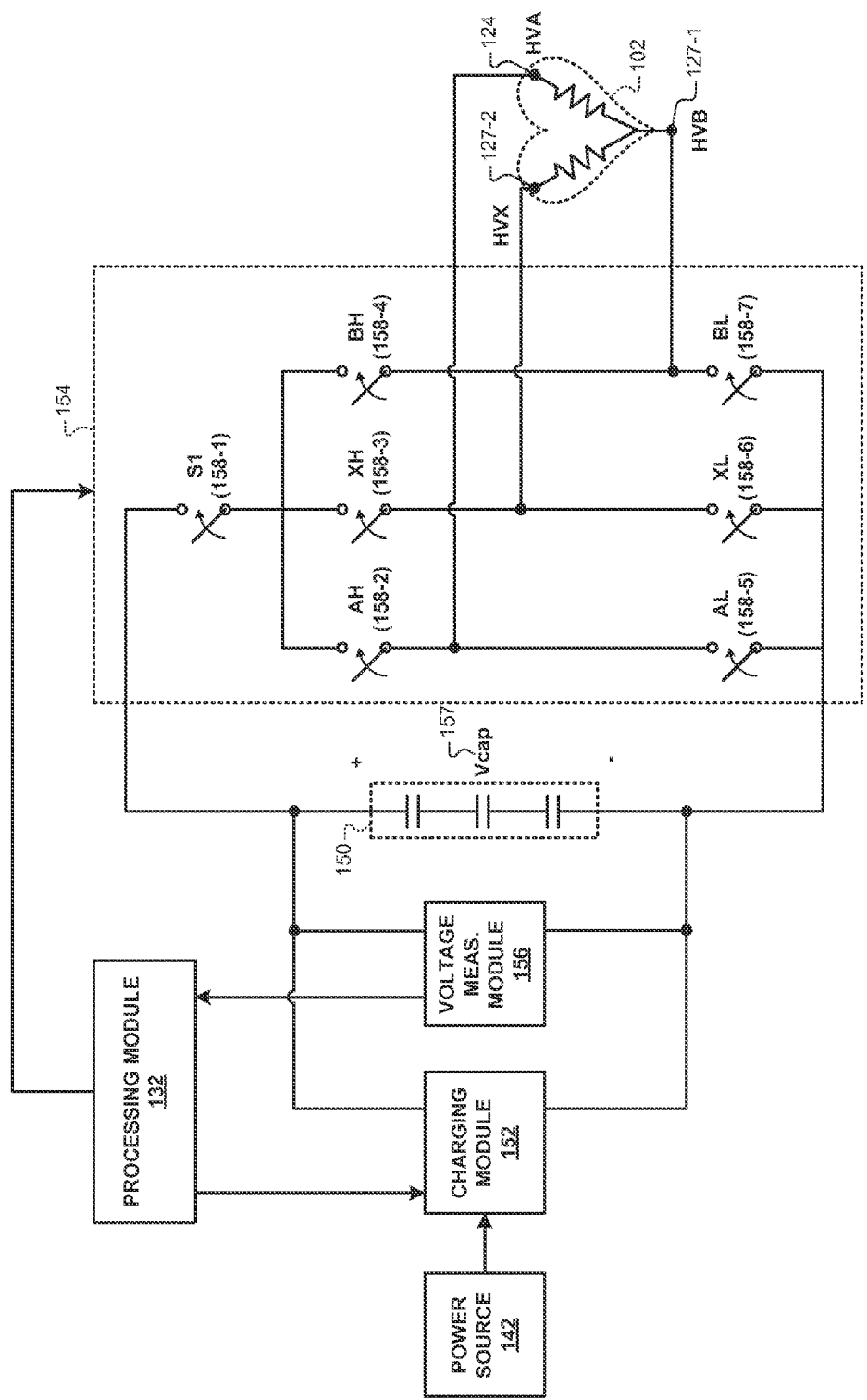
FIG. 4 shows example components of the IMD of FIG. 3 that control charging of high-voltage capacitors, monitoring of the voltage across the high-voltage capacitors, and delivery of high-energy therapy to the heart of the patient.
Figure 14:
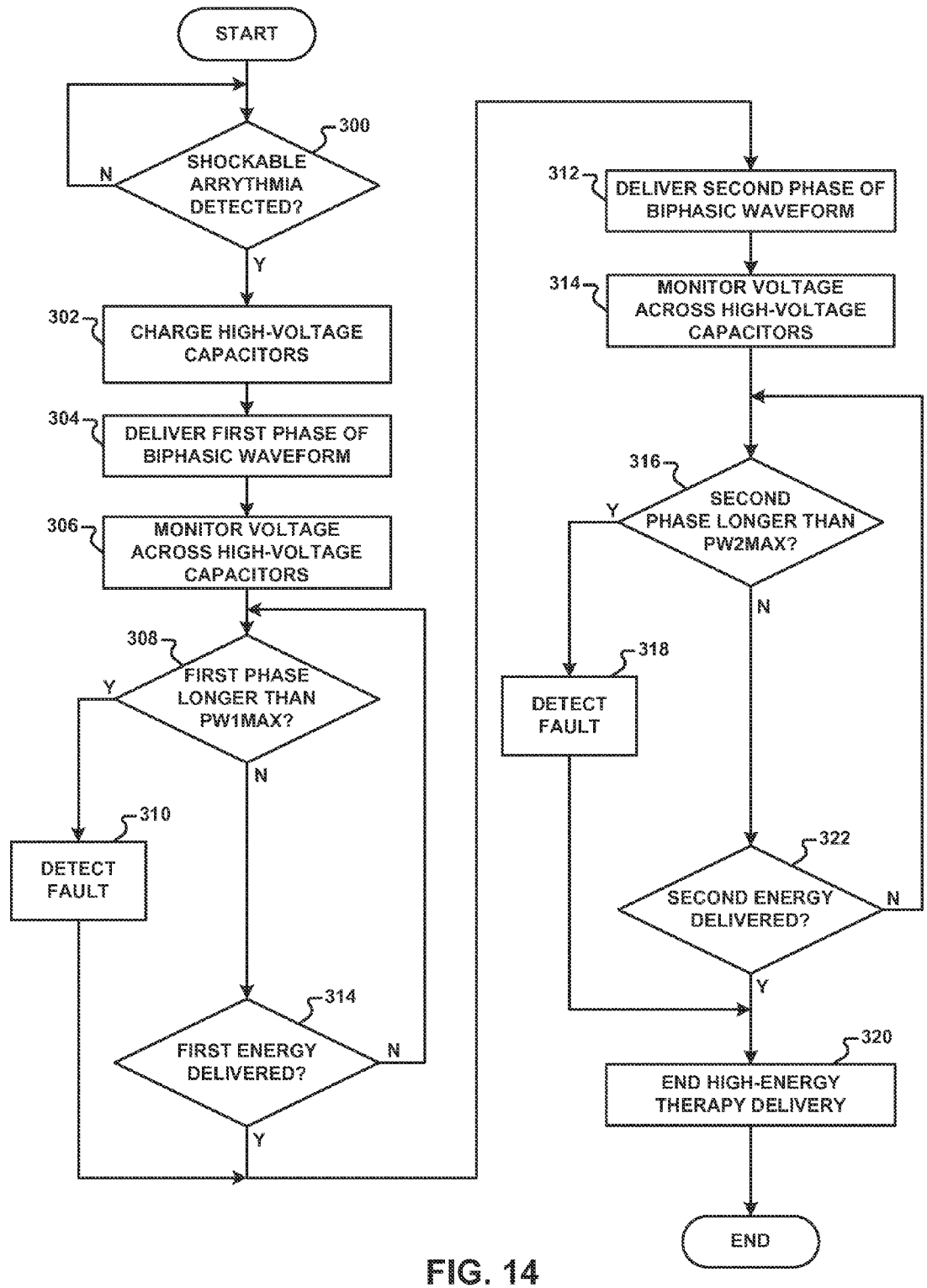
FIG. 14 is a flowchart that illustrates an example method for detecting high impedance faults during delivery of high-energy therapy using a biphasic waveform.
Figure 15:
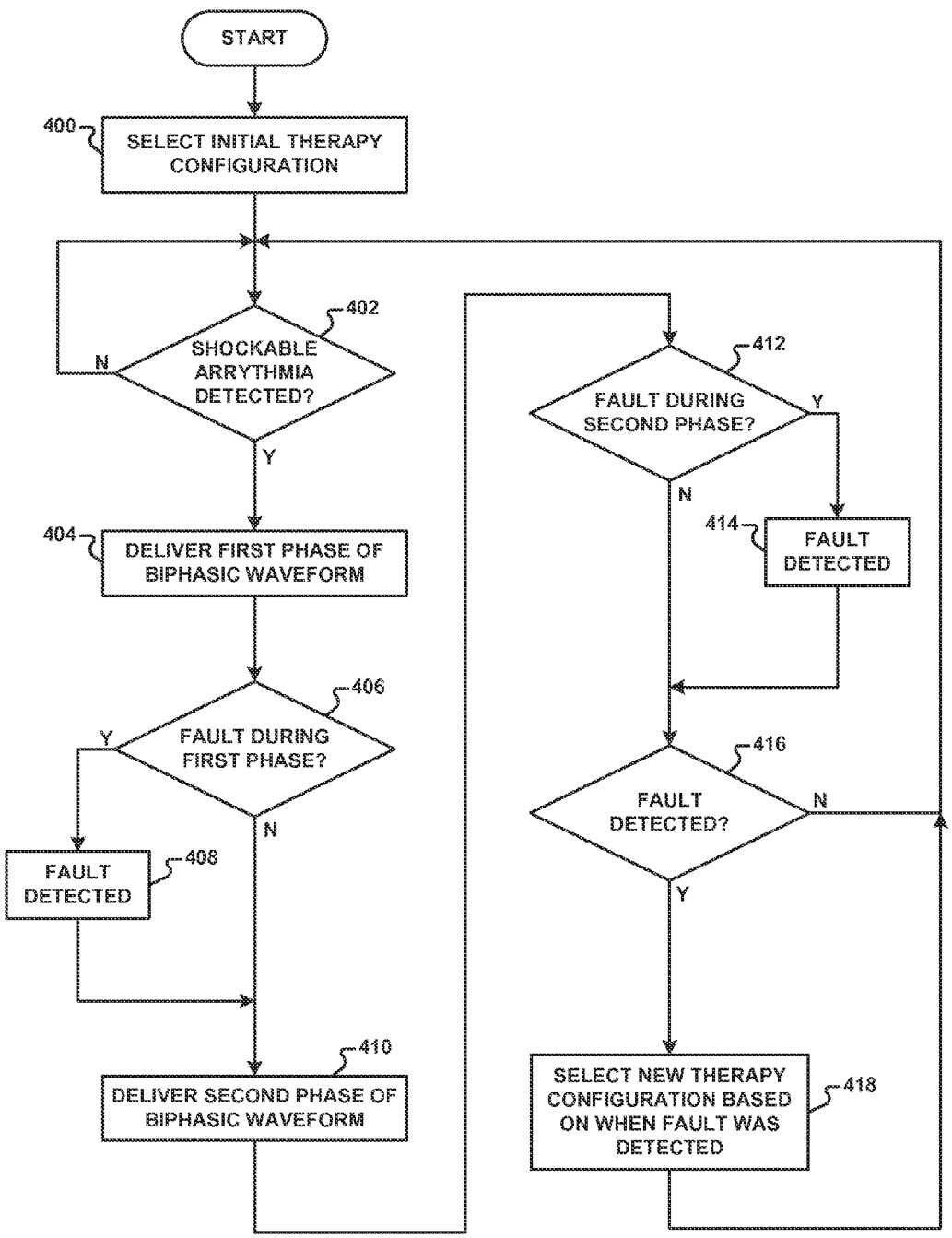
FIG. 15 is a flowchart that illustrates an example method for selecting new therapy configurations based on detection of a high impedance fault during previous deliveries of high-energy therapy.
Figure 16:
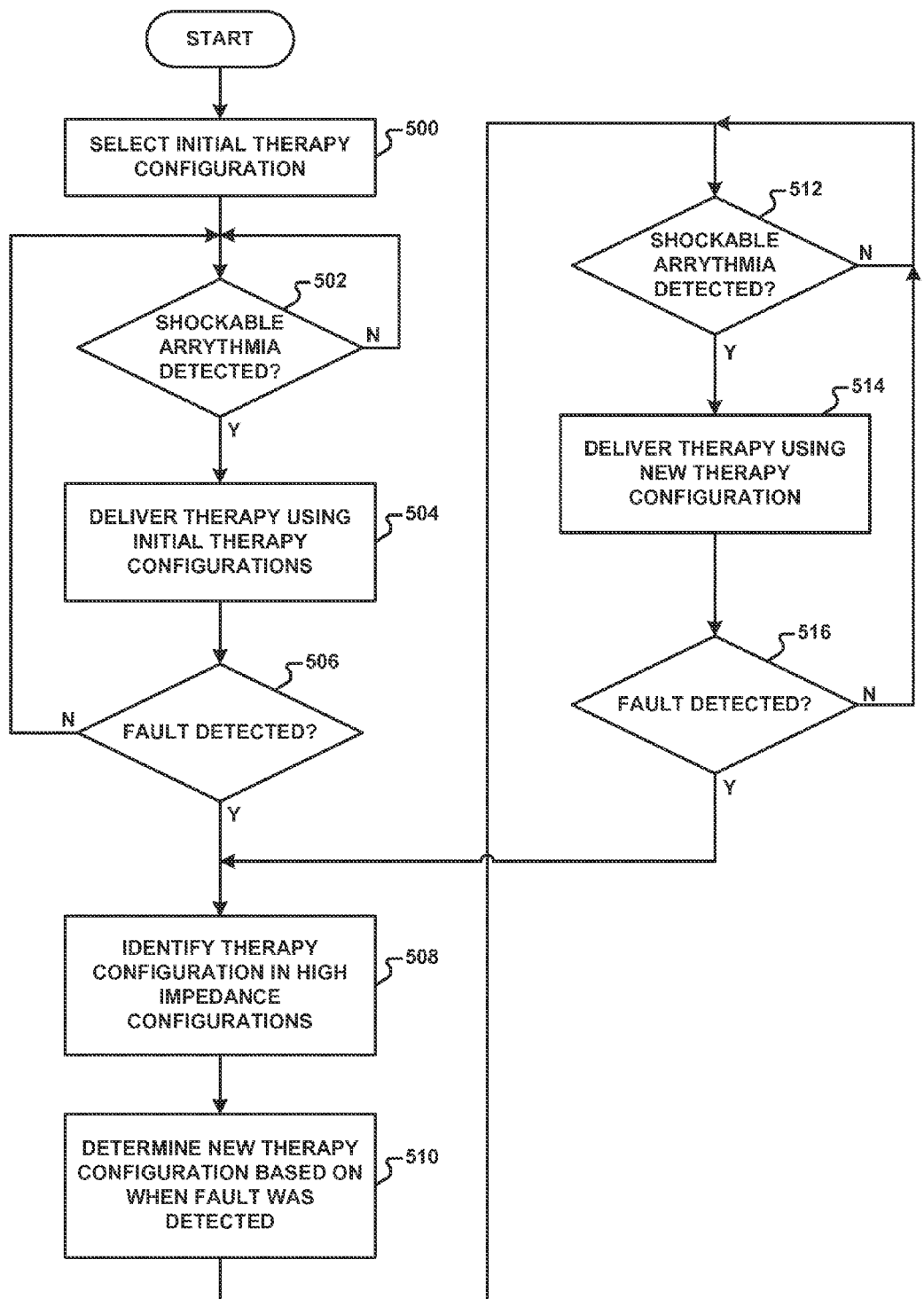
FIG. 16 is a flowchart that illustrates another example method for selecting new therapy configurations in response to detection of high impedance faults.
Figure 17:
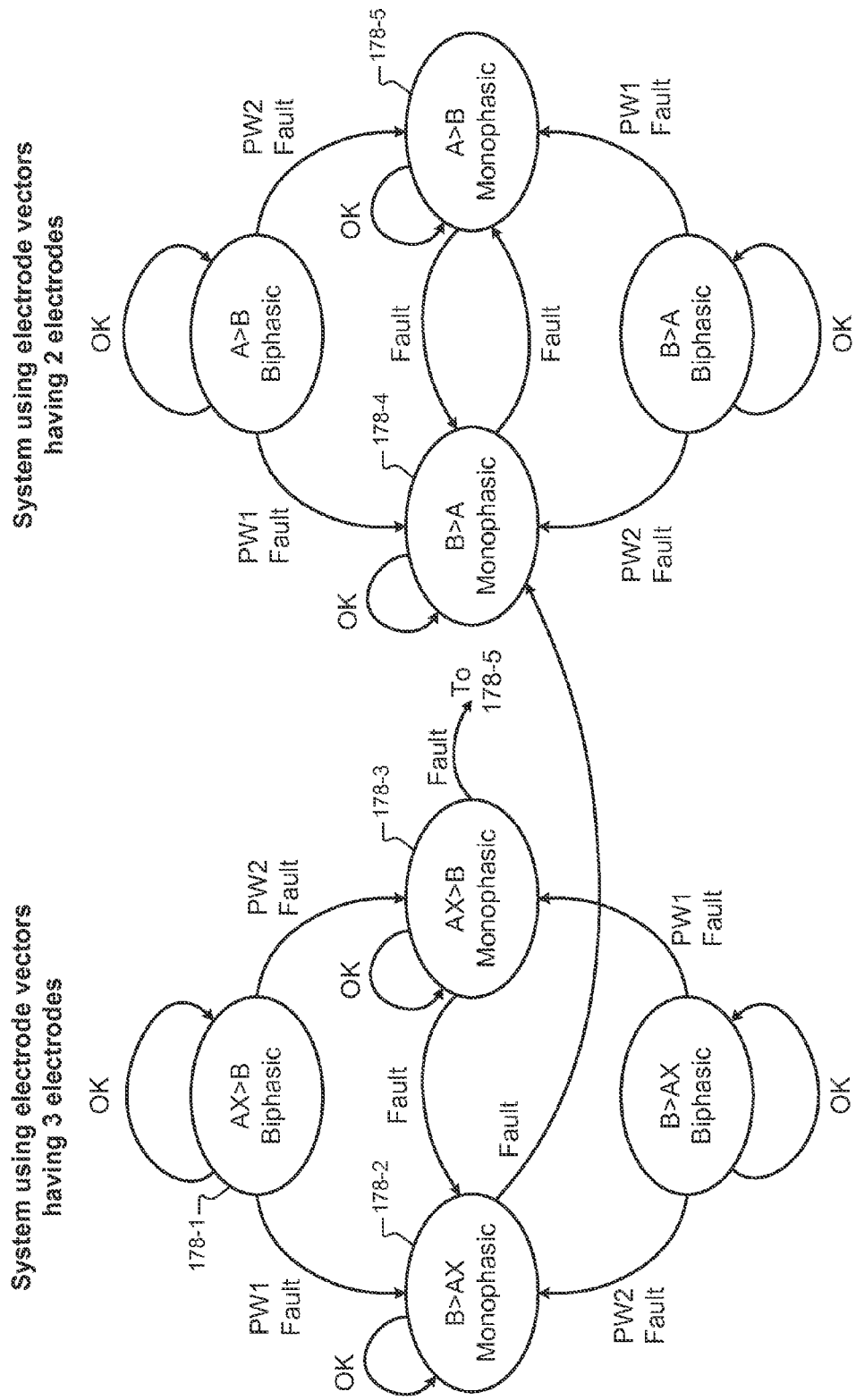
FIG. 17 is a state diagram that graphically illustrates example high impedance therapy configurations that may be selected by the IMD of FIG. 1 in response to detection of a high impedance fault.
Figure 18:
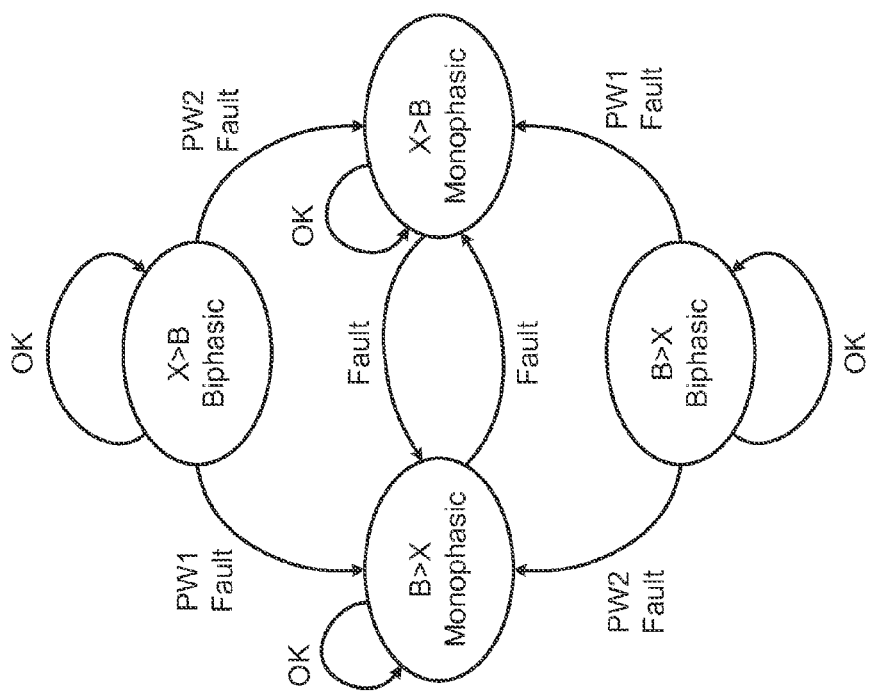
FIG. 18 is a state diagram that graphically illustrates another set of example high impedance therapy configurations that may be selected by the IMD of FIG. 1 in response to detection of a high impedance fault.

FIGS. 1-2 show an example system including an IMD that may deliver high-energy therapy, detect high impedance faults, and reconfigure therapy configurations in response to detection of the high impedance faults. FIG. 3 shows an example functional block diagram of the IMD of FIGS. 1-2 including a memory that stores initial therapy configurations and high impedance therapy configurations. FIG. 4 shows components of the IMD that control the delivery of high-energy therapy. FIGS. 5-9 illustrate biphasic and monophasic waveforms, the switching configurations used to deliver the waveforms, and a method for delivering the waveforms. FIGS. 10-13 show schematics of high impedance faults and possible changes in the first and second phases of a bipolar waveform caused by the high impedance faults. FIGS. 14-16 show methods for detecting high impedance faults and reconfiguring therapy configurations in response to detection of the high impedance faults. FIGS. 17-18 are state diagrams that describe how the IMD may transition between various therapy configurations based on when faults are detected during delivery of high-energy therapy. FIGS. 19-20 show potential delivery path faults and potential reconfiguration options for such faults.

FIG. 1 shows an example system 100 that may be used to diagnose conditions of and provide therapy to a heart 102 of a patient 104. System 100 includes an IMD 106. For example, IMD 106 may be an implantable pacemaker, cardioverter, and/or defibrillator that monitors electrical activity of heart 102 and provides electrical stimulation to heart 102.

IMD 106 includes a housing 108 and a connector block 110. Housing 108 and connector block 110 may form a hermetic seal that protects components of IMD 106. IMD 106 is coupled to leads 112, 114, and 116 via connector block 110. Leads 112, 114, 116 extend into heart 102. Right ventricular lead 114 extends into right ventricle 118. Left ventricular coronary sinus lead 116 extends into the coronary sinus to a region adjacent to the free wall of left ventricle 120. Right atrial lead 112 extends into right atrium 122.

Housing 108 may enclose an electrical sensing module that monitors electrical activity of heart 102, and may also enclose a signal generator module that generates therapeutic stimulation, such as cardiac pacing pulses, ATP therapy, cardioversion therapy, and/or defibrillation therapy. Leads 112, 114, 116 are coupled to the signal generator module and the electrical sensing module of IMD 106 via connector block 110.

FIG. 2 shows a more detailed view of IMD 106 and leads 112, 114, 116. IMD 106 includes a housing electrode 124, which may be referred to as HVA electrode 124 or CAN electrode 124, which may be formed integrally with an outer surface of housing 108 of IMD 106 or otherwise coupled to housing 108. Although a single housing electrode 124 is illustrated in FIGS. 1-2, IMD 106 may include more or less than a single housing electrode 124.

Leads 112, 114, 116 include electrodes 126-1 to 126-6 (collectively "electrodes 126"). Lead 114 includes bipolar electrodes 126-1, 126-2 which are located in right ventricle 118. Lead 116 includes bipolar electrodes 126-3, 126-4 which are located in coronary sinus 128. Lead 112 includes bipolar electrodes 126-5, 126-6 which are located in right atrium 122. Electrodes 126-1, 126-3, 126-5 may take the form of ring electrodes. Electrodes 126-2, 126-4, 126-6 may take the form of, for example, helix tip electrodes or small circular electrodes at the tip of a tined lead or other fixation element. Lead 114 includes elongated electrodes 127-7, 127-2 (collectively "electrodes 127") which may be coil electrodes. Electrode 127-1 may be referred to as HVB electrode 127-1 or as a right ventricular coil (RVC) electrode, and electrode 127-2 may be referred to as HVX electrode 127-2 or as a superior vena cava (SVC) coil electrode. Although three leads 112, 114, 116 are illustrated, systems according to the present disclosure may be implemented using more or less than 3 leads. Additionally, systems according to the present disclosure may be implemented using additional or fewer electrodes than illustrated in FIGS. 1-2, e.g. such as one or more epicardial patch electrodes or coronary sinus electrodes.

IMD 106 may sense electrical activity of heart 102 and/or deliver electrical stimulation to heart 102 via electrodes 124, 126, 127. IMD 106 may sense electrical activity using any combination of electrodes 124, 126, 127. For example, IMD 106 may sense electrical activity via any bipolar combination of electrodes 126, 127. Furthermore, any of electrodes 126, 127 may be used for unipolar sensing in combination with housing electrode 124. IMD 106 may deliver pacing pulses using a unipolar or bipolar combination of electrodes 124, 126, 127. IMD 106 may deliver high-energy therapy (e.g., cardioversion pulses and/or defibrillation pulses) to heart 102 via any combination of elongated electrodes HVB 127-1, HVX 127-2, and housing electrode HVA 124.

Using the signal generator module and the electrical sensing module, IMD 106 may provide pacing pulses to heart 102 based on the electrical signals sensed within heart 102. IMD 106 may also provide ATP therapy, cardioversion, and/or defibrillation therapy to heart 102 based on the electrical signals sensed within heart 102. For example, IMD 106 may detect an arrhythmia of heart 102, such as VT/VF, and deliver ATP therapy, cardioversion, or defibrillation therapy to heart 102 in response to the detection of VT/VF.

Referring back to FIG. 1, system 100 may include a programmer 130. Programmer 130 may be a handheld computing device, desktop computing device, a networked computing device, etc. Programmer 130 may include a computer-readable storage medium having instructions that cause a processor of programmer 130 to provide the functions attributed to programmer 130 in the present disclosure. Programmer 130 may include a telemetry head (not shown). IMD 106 and programmer 130 may wirelessly communicate with one another, e.g., transfer data between one another, via the telemetry head. For example, IMD 106 may send data to programmer 130, and programmer 130 may retrieve data stored in IMD 106 and/or program IMD 106.

Data retrieved from IMD 106 using programmer 130 may include cardiac EGMs stored by IMD 106 that indicate electrical activity of heart 102 and marker channel data that indicates the occurrence and timing of sensing, diagnosis, and therapy events associated with IMD 106. Additionally, data may include information regarding the performance or integrity of IMD 106 or other components of diagnostic system 100, such as leads 112, 114, 116, or a power source of IMD 106. For example, data may include information regarding whether any high impedance faults were detected during delivery of high-energy therapy, and in some examples, which therapy configurations resulted in detection of high impedance faults. Data transferred to IMD 106 using programmer 130 may include, for example, values for operational parameters, electrode vectors used to deliver high-energy therapy, waveforms used for delivery of high-energy therapy, a total amount of energy used during high-energy therapy, and the distribution of the total energy among the phases of delivery for a biphasic defibrillation waveform.

FIG. 3 shows a functional block diagram of an example IMD 106. IMD 106 includes a processing module 132, memory 134, a signal generator module 136, an electrical sensing module 138, a communication module 140, and a power source 142, such as a battery, e.g., a rechargeable or non-rechargeable battery. In some examples, IMD 106 may include one or more sensors (e.g., sensor 144) with which processing module 132 may communicate. For example, sensor 144 may comprise at least one of a motion sensor (e.g., an accelerometer or piezoelectric element) and a heart sound sensor. Processing module 132 may determine, for example, an activity level of patient 104 and a heart rate of patient 104 based on data measured by sensor 144.

Modules included in IMD 106 represent functionality that may be included in IMD 106 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Processing module 132 may communicate with memory 134. Memory 134 may include computer-readable instructions that, when executed by processing module 132, cause processing module 132 to perform the various functions attributed to processing module 132 herein. Memory 134 may include any volatile, non-volatile, magnetic, or electrical media, such as RAM, ROM, NVRAM, EEPROM, Flash memory, or any other digital media.

Processing module 132 may communicate with signal generator module 136 and electrical sensing module 138. Signal generator module 136 and electrical sensing module 138 are electrically coupled to electrodes 126, 127 of leads 112, 114, 116 and housing electrode 124. Electrical sensing module 138 is configured to monitor signals from electrodes 124, 126, 127 in order to monitor electrical activity of heart 102. Electrical sensing module 138 may selectively monitor any bipolar or unipolar combination of electrodes 124, 126, 127.

Signal generator module 136 may generate and deliver electrical stimulation therapy to heart 102 via electrodes 124, 126, 127. Electrical stimulation therapy may include at least one of pacing pulses, ATP therapy, cardioversion therapy, and defibrillation therapy. Processing module 132 may control signal generator module 136 to deliver electrical stimulation therapy to heart 102 according to one or more therapy programs, which may be stored in memory 134. For example, processing module 132 may control signal generator module 136 to deliver pacing pulses to heart 102 based on one or more therapy programs and signals received from electrical sensing module 138. In other examples, processing module 132 may control signal generator module 136 to deliver at least one of ATP therapy, cardioversion therapy, and defibrillation therapy when processing module 132 detects a tachyarrhythmia. For example, in the event that processing module 132 detects a tachyarrhythmia, processing module 132 may load an ATP regimen from memory 134, and control signal generator module 136 to implement the ATP regimen. In other examples, processing module 132 may implement a cardioversion regimen or a defibrillation regimen upon detection of a tachyarrhythmia.

Communication module 140 includes any suitable hardware, firmware, software or any combination thereof for communicating with another device, such as programmer 130 and/or a patient monitor. Under the control of processing module 132, communication module 140 may receive downlink telemetry from and send uplink telemetry to programmer 130 and/or a patient monitor with the aid of an antenna (not shown) in IMD 106.

Processing module 132 may receive raw data (e.g., digitized electrogram data) from electrical sensing module 138 and detect cardiac events based on the raw data. For example, processing module 132 may analyze the raw data and detect arrhythmias (e.g., VT/VF) using any suitable arrhythmia detection algorithm. In one example, processing module 132 may detect tachyarrhythmias using a rate-based detection algorithm in which processing module 132 monitors R-R intervals and identifies a tachyarrhythmia when a predetermined ratio of R-R intervals are shorter than a threshold interval. In some examples, processing module 132 may perform further analysis of tachyarrhythmias using rate information. For example, processing module 132 may characterize tachyarrhythmias based on the range of values in which the intervals fall, the stability of the intervals, and the average or median values of the intervals. In some examples, processing module 132 may confirm the presence of detected tachyarrhythmias using other algorithms such as a template matching algorithms.

Processing module 132 may instruct signal generator module 136 to deliver high-energy therapy (e.g., defibrillation pulses or cardioversion pulses) in response to detection of shockable arrhythmias (e.g., VT/VF). Delivery of high-energy therapy by signal generator module 136 to heart 102 may correct the shockable arrhythmia and return heart 102 to a normal rhythm. In examples where the detected shockable arrhythmia is not corrected, processing module 132 controls delivery of subsequent high-energy therapies.

Signal generator module 136 includes circuits that deliver the high-energy therapy to heart 102 and monitor the delivery of the high-energy therapy while the high-energy therapy is being delivered. FIG. 3 shows a high-level functional block diagram of signal generator module 136. Signal generator module 136 may include an energy storage device for storing energy to be delivered during the high-energy therapy. The energy storage device described herein includes one or more capacitors, hereinafter "high-voltage capacitors 150," that are used to store electrical charge for delivery to heart 102 during high-energy therapy. Although the energy storage device used to store energy for delivery of high-energy therapy is described herein as one or more capacitors, other energy storage devices may be implemented.

Signal generator module 136 may also include a charging module 152, a switching circuit 154, and a voltage measuring module 156. Charging module 152 may charge high voltage capacitors 150 in response to instructions from processing module 132, e.g., instructions provided by processing module 132 in response to detection of a shockable arrhythmia. Voltage measuring module 156 may measure the voltage across high-voltage capacitors 150 in order to determine a level of charge present on high-voltage capacitors 150. Switching circuit 154 may be controlled by processing module 132 in order to deliver the high-energy therapy to heart 102 via leads 112, 114, 116. In other words, under control of processing module 132, switching circuit 154 may connect high-voltage capacitors 150 to electrodes 124, 127 in order to transfer energy from high-voltage capacitors 150 to heart 102.

Typical operation of IMD 106 with respect to the delivery of high-energy therapy, e.g., without detection of high impedance faults, is described hereinafter with respect to the functional block diagrams of FIGS. 4-8 and the method of FIG. 9.

FIG. 4 shows components of IMD 106 that control charging of high-voltage capacitors 150, monitoring of the voltage across high-voltage capacitors 150, and delivery of high-energy therapy to heart 102. Processing module 132, upon detection of a shockable arrhythmia (e.g., VT/VF) may instruct charging module 152 to charge high-voltage capacitors 150 using energy from power source 142. High-voltage capacitors 150 may store the energy that is to be subsequently delivered to heart 102 during delivery of the high-energy therapy. Charging module 152 may include a DC-to-DC converter circuit that converts a source of direct current from one voltage level to another. In some examples, the DC-to-DC converter may have a flyback topology.

Voltage measuring module 156 may measure the voltage across high-voltage capacitors 150 while high-voltage capacitors 150 are being charged by charging module 152. The voltage that may be measured across high-voltage capacitors 150 is indicated by +/−Vcap at 157 in FIG. 4. The voltage measured across high-voltage capacitors 150 may indicate an amount of electrical energy stored on high-voltage capacitors 150. Voltage measuring module 156 may indicate the measured voltage to processing module 132. Processing module 132 may determine an amount of energy stored by high-voltage capacitors 150 based on the voltage indicated by voltage measuring module 156. For example, processing module 132 may include a look-up table (e.g., voltage vs. energy) or an equation that processing module 132 may use to determine the amount of energy stored by high-voltage capacitors 150 based on the voltage measured across high-voltage capacitors 150.

In some examples, voltage measuring module 156 may include analog-to-digital conversion circuits that measure the voltage across high-voltage capacitors 150 and generate a digital value that indicates the measured voltage. In these examples, processing module 132 may determine the voltage across high-voltage capacitors 150 based on the digital value received from voltage measuring module 156.

Processing module 132 may instruct charging module 152 to stop charging high-voltage capacitors 150, e.g., disconnect from high-voltage capacitors 150, when the voltage across high-voltage capacitors 150 reaches a threshold voltage that indicates that high-voltage capacitors 150 have been charged with an amount of electrical energy to be used during delivery of high-energy therapy. The total amount of energy to be delivered during high-energy therapy may be programmed into memory 134 by a clinician, e.g., using programmer 130. In some examples, processing module 132 may determine the threshold voltage based on the programmed energy. Based on the determined threshold voltage, processing module 132 may determine when the programmed energy is stored on high-voltage capacitors 150 during charging. The threshold voltage that indicates that high-voltage capacitors 150 are charged to a state in which high-voltage capacitors 150 may deliver the high-energy therapy may be indicated as $V_0$ in FIG. 5 and FIG. 8. In terms of FIG. 4, processing module 132 may instruct charging module 152 to charge high-voltage capacitors 150 until the voltage Vcap 157 across high-voltage capacitors 150 reaches the threshold voltage $V_0$.

After high-voltage capacitors 150 are charged up to the threshold voltage $V_0$ and processing module 132 instructs charging module 152 to stop charging high-voltage capacitors 150, processing module 132 controls switching circuit 154 to deliver the high-energy therapy to heart 102. Switching circuit 154 includes switches 158-1, 158-2, ..., and 158-7 (collectively "switches 158"). Each of switches 158, when functional, may operate in one of an "open state" or a "closed state." Each of switches 158 may act as an open circuit (i.e., a high impedance) when operating in the open state. Each of switches 158 may act as a short circuit (i.e., a low impedance) when operating in the closed state. In some examples, a switch operating in the "closed state" may be referred to as operating in the "on state" or may be referred to as "turned on." In a similar manner, a switch operating in the "open state" may be referred to as operating in the "off state" or may be referred to as "turned off."

When switches 158 are functional, the state of switches 158 (i.e., open or closed) may be controlled by processing module 132. The collective state of all switches 158 may be referred to as a "switching configuration" of switching circuit 154. Accordingly, processing module 132 may control the switching configuration of switching circuit 154. In some examples, one or more of switches 158 may malfunction. A malfunction in a switch may refer to a scenario where the actual behavior of the switch is different from the behavior of the switch that was commanded by processing module 132. In some examples, a malfunctioning switch will remain in an open state when instructed to close. In other examples, a malfunctioning switch will remain in a closed state when instructed to open. In other words, a malfunctioning switch may be stuck in one of the open or closed states. A malfunctioning switch may not necessarily behave in either a strictly open state (i.e., an open circuit) or a strictly closed state (i.e., as a short circuit), but may behave as an impedance that has a value somewhere between the impedances of the closed and open states.

Switches 158 may include one or more types of switching technologies. Switches 158 may generally represent any type of switching device that may be instructed to operate in open/closed states and that may operate under conditions (e.g., voltages/currents) present during delivery of high-energy therapy. In some examples, switches 158 may be silicon-controlled rectifier (SCR) devices. In examples where switches 158 include SCR devices, processing module 132 may apply a control voltage to the SCR devices to turn on the SCR devices. In other examples, switches 158 may include types of switches other than SCR devices. For example, switches 158 may include power metal-oxide-semiconductor field-effect-transistors (MOSFETs). In examples where switches 158 include power MOSFETs, processing module 132 may control a gate voltage applied to switches 158 to control the states of switches 158. Although switches 158 may include SCR devices and power MOSFET devices, in other examples, switches 158 may include other types of high power switching devices, such as insulated-gate bipolar transistors (IGBTs), TRIACS, thyristors, or other power switching devices.

Generally, processing module 132 may control delivery high-energy therapy to heart 102 based on a variety of parameters. The parameters that specify delivery of high-energy therapy may be referred to herein as high-energy therapy configurations, or simply therapy configurations. As described above, therapy configurations may specify an electrode vector to be used during therapy and an electrical waveform (e.g., biphasic or monophasic) to be delivered by the electrode vector.

Memory 134 may store the various therapy configurations that may be implemented by processing module 132 in order to deliver high-energy therapy. Processing module 132 may, in response to detection of a shockable arrhythmia, retrieve a therapy configuration from memory 134, and control the delivery of high-energy therapy based on the information included in the retrieved therapy configuration. As illustrated in FIG. 3, memory 134 may include two sets of therapy configurations, initial therapy configurations 160, and high impedance therapy configurations 162.

Initially, processing module 132 may control the delivery of high-energy therapy using initial therapy configurations 160. Initial therapy configurations 160 may define a pattern of selection of therapy configurations to be used by processing module 132 in scenarios where processing module 132 has not previously detected a high impedance fault during delivery of high-energy therapy. Accordingly, processing module 132 may control delivery of high-energy therapy according to initial therapy configurations 160 in response to detection of a shockable arrhythmia in scenarios where processing module 132 has not yet detected a high impedance fault.

Initial therapy configurations 160 may define a pattern of selection of therapy configurations that may be used by processing module 132 during attempts to treat a detected shockable arrhythmia. For example, processing module 132 may initially attempt to treat a shockable arrhythmia using a first therapy configuration of initial therapy configurations 160. If successful in treating the shockable arrhythmia, processing module 132 may return to monitoring the rhythm of heart 102. If unsuccessful in treating the shockable arrhythmia, e.g., if the shockable arrhythmia is not corrected, processing module 132 may select a second therapy configuration of initial therapy configurations 160 to treat the shockable arrhythmia. In this manner, processing module 132 may continue to select consecutive therapy configurations from initial therapy configurations 160 in order to attempt to treat a shockable arrhythmia in different ways until a successful treatment is found, e.g., until the shockable arrhythmia is corrected.

Initial therapy configurations 160 may be programmed into memory 134 prior to implantation, e.g., as factory default settings or programmed by a clinician. In other examples, initial therapy configurations 160 may be updated by a clinician using programmer 130 after IMD 106 is implanted. Initial therapy configurations 160 may define a variety of different electrode vector and waveform combinations, as well as different amounts of energies to be delivered during high-energy therapy.

Processing module 132 may control delivery of high-energy therapy according to initial therapy configurations 160 until a high impedance fault is detected during delivery of high-energy therapy according to initial therapy configurations 160. Upon detection of a high impedance fault during delivery of high-energy therapy, processing module 132 may begin delivering high-energy therapy according to high impedance therapy configurations 162 stored in memory 132. High impedance therapy configurations 162 may define the selection of therapy configurations used by processing module 132 after a high impedance fault is detected during delivery of high-energy therapy. Accordingly, after detection of a high impedance fault, processing module 132 may control delivery of high-energy therapy according to high impedance therapy configurations 162 in response to detection of a shockable arrhythmia.

High impedance therapy configurations 162 may represent a plurality of different therapy configurations (i.e., N different therapy configurations). Each of the N therapy configurations 164-1, 164-2, . . . , 164-N (collectively "N therapy configurations 164") may define an electrode vector (e.g., AX>B, A>X, etc.), a waveform (e.g., biphasic/monophasic), and transition data. Transition data included in each of N therapy configurations 164 may define a subsequent one of the N therapy configurations to select in response to detection of a high impedance fault at the current therapy configuration. For example, if processing module 132 detects a high impedance fault while using first therapy configuration 164-1, processing module 132 may select a subsequent therapy configuration to use by looking at the transition data that is associated with the current therapy configuration 164-1. The transition data of first therapy configuration 164-1 may indicate that processing module 132 should transition to second therapy configuration 164-2 in response to detection of a high impedance fault during delivery according to first therapy configuration 164-1. In this case, processing module 132 may then control high-energy therapy delivery according to second therapy configuration 164-2. If a fault is then detected by processing module 132 when using second therapy configuration 164-2, processing module 132 may set the next therapy configuration to the therapy configuration indicated by the transition data of second therapy configuration 164-2. In this manner, processing module 132 may determine a subsequent therapy configuration to use for the delivery of high-energy therapy based on the current therapy configuration in which a high impedance fault is detected.

In addition to determining subsequent therapy configurations based on a current therapy configuration in which a high impedance fault is detected, processing module 132 may also make the subsequent therapy selection based when the high impedance fault was detected during the delivery of high-energy therapy. Accordingly, processing module 132 may select a subsequent therapy configuration based on the current therapy configuration in which a fault is detected and based on when the detected fault occurred during delivery of high-energy therapy according to the current therapy configuration.

The transition data may specify the subsequent therapy configuration based on when the high impedance fault was detected during the current therapy configuration. For example, the transition data associated with first therapy configuration 164-1 may instruct processing module 132 to deliver therapy according to second therapy configuration 164-2 if a high impedance fault is detected during the first phase of the biphasic waveform of first therapy configuration 164-1, and the transition data associated with first therapy configuration 164-1 may instruct processing module 132 to deliver therapy according to the Nth therapy configuration 164-N if a high impedance fault is detected during the second phase of the biphasic waveform of first therapy configuration 164-1. Selection of therapies according to high impedance therapy configurations 162 is described further with respect to the state diagrams of FIGS. 17-18, for example.

Although initial therapy configurations 160 and high impedance therapy configurations 162 are illustrated as separate therapy configurations, some therapy configurations included in initial therapy configurations 160 may be the same as some therapy configurations included in high impedance therapy configurations 162. The illustration of the therapy configurations 160, 162 as separate is meant to convey the concept that processing module 132 may follow different paths when selecting therapy configurations, depending on whether a high impedance fault has been detected.

An electrode vector specified by a therapy configuration may include two or three of electrodes 124, 127. In some examples, three electrodes may be used to deliver high-energy therapy, while in other examples, less than three electrodes may be used to deliver high-energy therapy, i.e., in some examples, only 2 electrodes may be used to deliver therapy while a third electrode does not deliver therapy or is not physically present in the system.

Electrodes used for delivery of defibrillation therapy are described and illustrated herein as electrodes HVA 124, HVB 127-1, and HVX 127-2. Electrode HVA 124 is an electrode on housing 108, and may be referred to as a "can electrode" in some examples. Electrode HVB 127-1 is a defibrillation coil in right ventricle 118. Electrode HVX 127-2 is an additional electrode on lead 114 or may be part of an additional lead or electrode in the system. Although electrodes HVA 124, HVB 127-1, and HVX 127-2 are described herein as electrodes used for the delivery of high-energy therapy, it is contemplated that other electrode configurations different from that illustrated and described herein may be used for delivery of high-energy therapy.

Electrode vectors may be described and illustrated using a notation that includes the greater-than symbol ">" to indicate the direction of current between electrodes. For example, electrode vector "AX>B" indicates that the direction of current during therapy delivery is from HVA electrode 124 and HVX electrode 127-2 to HVB electrode 127-1. In some examples, e.g., during biphasic or multiphasic delivery, the direction of current may be reversed or altered based on the phase of delivery. Electrode vectors described herein that include three electrodes include "AX>B" and "B>AX." Electrode vectors described herein that include only two electrodes include "A>B", "B>A", "X>B", and "B>X."

Figure 5:
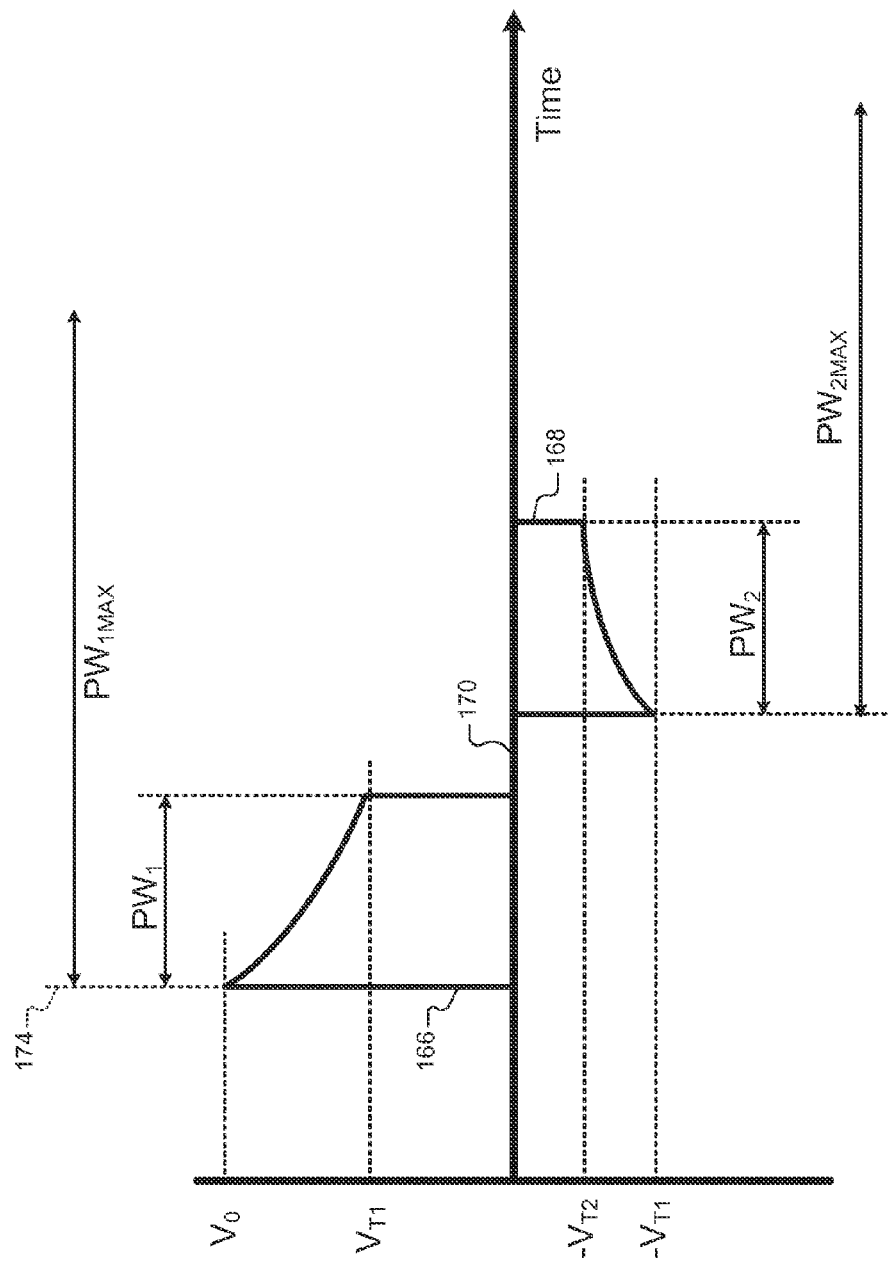
FIG. 5 shows a biphasic waveform that includes a first phase of delivery and a second phase of delivery which are separated by a transition period.
Figure 8:
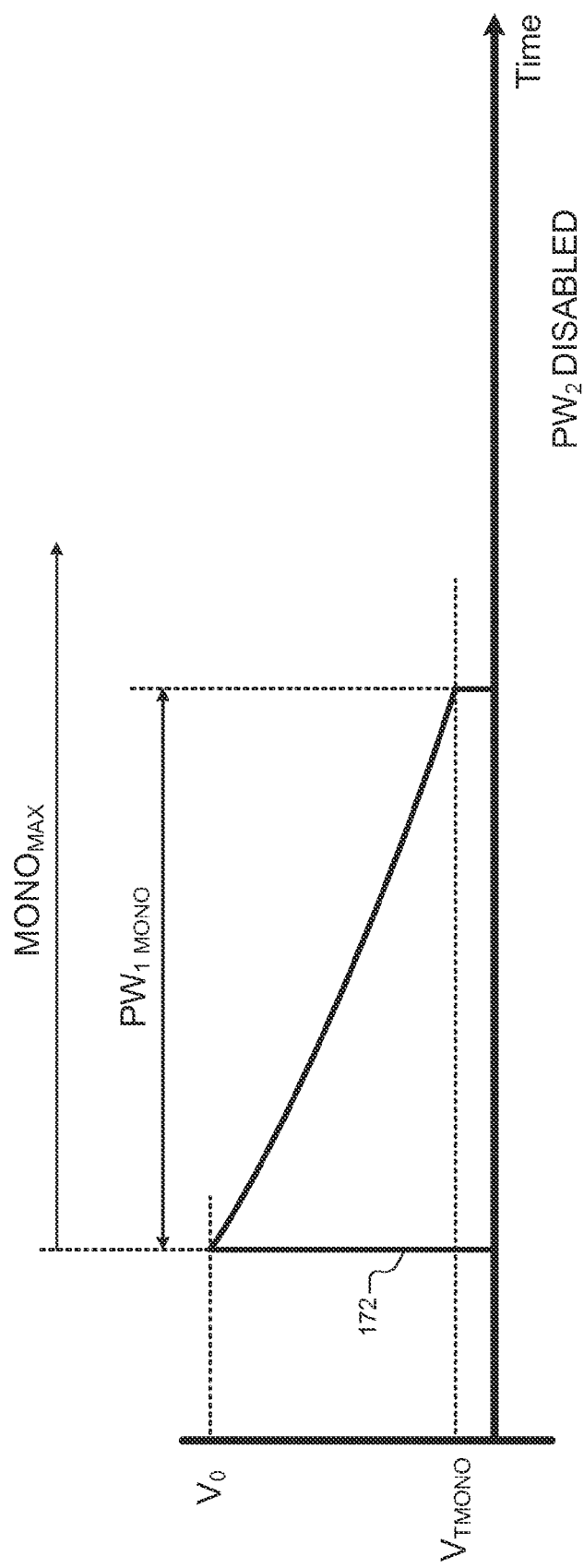
FIG. 8 shows an example monophasic waveform.

Therapy configurations may define the type of waveform to be delivered during high-energy therapy. Processing module 132 may control switching circuit 154 to deliver the type of waveform defined by the therapy configurations 160, 162. Generally, high-energy therapy may be delivered using a biphasic waveform or a monophasic waveform. Example biphasic and monophasic waveforms are illustrated in FIGS. 5 and 8, respectively. The biphasic waveform illustrated in FIG. 5 includes a first phase 166 and a second phase 168, separated by a transition period 170. The monophasic waveform illustrated in FIG. 8 includes a single phase 172, referred to herein as a "monophasic pulse 172." Delivery of high-energy therapy according to the biphasic and monophasic waveforms is now described with respect to FIGS. 5 and 8, respectively.

Referring now to FIG. 5, a biphasic waveform includes a first phase of delivery 166 and a second phase of delivery 168, separated by a transition period 170. The biphasic waveform of FIG. 5 is illustrated as a voltage waveform vs. time. The y-axis may represent the magnitude of the voltage across high-voltage capacitors 150, while the x-axis may represent the amount of time elapsed during delivery of the biphasic waveform. Processing module 132 may start the delivery of high-energy therapy at 174. Prior to the start of high-energy therapy, charging module 152 charged high-voltage capacitors 150 to the voltage $V_0$, e.g., based on the amount of energy programmed by the clinician, as described above. Accordingly, the voltage across high-voltage capacitors 150 at the start of delivery of the high-energy therapy is set at $V_0$.

Figure 6:
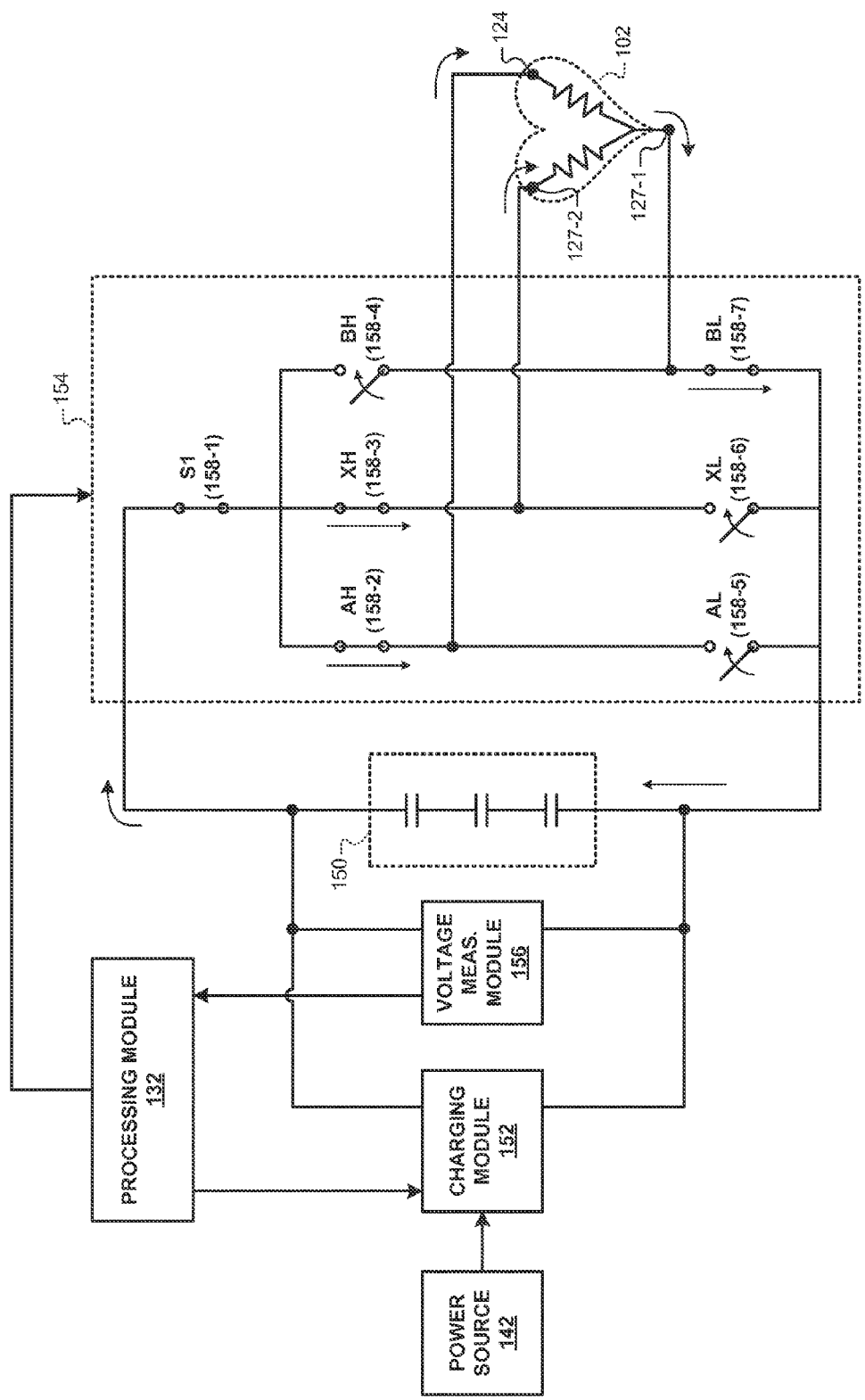
FIG. 6 is a schematic that illustrates an example switching configuration of a switching circuit that may be used to deliver a first phase of high-energy therapy.

Prior to delivery of high-energy therapy according to FIG. 5, switches 158 of switching circuit 154 may all be in the open state as illustrated in FIG. 4. Processing module 132 may instruct switching circuit 154 to change switching configurations in order to start delivery of first phase 166. FIG. 6 illustrates an example switching configuration of switching circuit 154 that may be used to deliver first phase 166 of high-energy therapy. In the example switching configuration of FIG. 6 instructed by processing module 132, first phase 166 of high-energy therapy is delivered using electrodes HVA 124, HVX 127-2, and HVB 127-1 (i.e., electrode vector AX>B). In order to deliver first phase 166, processing module 166 may instruct each of switches S1 158-1, AH 158-2, XH 158-3, and BL 158-7 to transition from the open state to the closed state.

The direction of current through switches AH 158-2, XH 158-3, BL 158-7 and heart 102 (modeled as resistors) during first phase 166 is illustrated by arrows. The voltage across high-voltage capacitors 150 may decrease during first phase 166 as current is delivered to heart 102. Voltage measuring module 156 may measure the voltage across high-voltage capacitors 150 during first phase 166. Processing module 132 may monitor the voltage measured by voltage measuring module 156 during first phase 166. Processing module 132 may determine the amount of energy delivered to heart 102 based on the change in the monitored voltage.

As described above, a clinician may program a total amount of energy to be delivered during the high-energy therapy. The clinician may also program how the total amount of energy is to be distributed between first and second phases 166, 168. In some examples, the clinician may program IMD 106 to divide the total amount of programmed energy equally (e.g., 50/50) between first and second phases 166, 168. In other examples, the clinician may program IMD 106 to divide the total amount of programmed energy unequally (e.g., 60/40) between the first and second phases 166, 168. Processing module 132 may determine threshold voltages for each of the first and second phases 166, 168 based on the amount of energy to be delivered during the first and second phases 166, 168, respectively. The threshold voltages of the first and second phases 166, 168 may be used by processing module 132 as indicators that the energy for each of the first and second phases 166, 168 has been delivered.

The threshold voltages for the first and second phases 166, 168 are illustrated as $V_{T1}$ and $-V_{T2}$ in FIG. 5. Processing module 132 may determine that the amount of energy programmed for first phase 166 (i.e., the first portion of the total energy) was delivered to heart 102 when the monitored voltage across high-voltage capacitors 150 has dropped from $V_0$ to $V_{T1}$. Similarly, processing module 132 may determine that the amount of energy programmed for second phase 168 (i.e., the second portion of the total energy) was delivered to heart 102 when the monitored voltage across high-voltage capacitors 150 has dropped from $V_{T1}$ to $V_{T2}$.

Processing module 132 may control switching circuit 154 to discontinue delivery of high-energy therapy when processing module 132 determines that the voltage across high-voltage capacitors 150 has dropped to the first threshold voltage $V_{T1}$. In other words, processing module 132 may set the switching configuration of switching circuit 154 such that high-voltage capacitors 150 are disconnected from electrodes 124, 127. In some examples, processing module 132 may instruct switching circuit 150 to open all switches 158 in switching circuit 154 so that high-voltage capacitors 150 are disconnected from electrodes 124, 127. In examples where switches AH 158-2, XH 158-3, and BL 158-7 are SCR devices and switch S1 158-1 is a power MOSFET device, processing module 132 may control switch S1 158-1 to open, thereby disconnecting switches AH 158-2, XH 158-3, and BL 158-7 from high-voltage capacitors 150 and therefore setting switches AH 158-2, XH 158-3, and BL 158-7 to the open state.

With respect to FIG. 8, processing module 132 may control delivery of monophasic pulse 172 in a similar manner that processing module 132 controls delivery of first phase 166 described above. As illustrated in FIG. 8, processing module 132 may include a threshold voltage $V_{TMONO}$ that may be used by processing module 132 to determine when to discontinue therapy.

Referring again to FIG. 5, processing module 132 may wait for a short transition period 170 after first phase 166 prior to controlling switching circuit 154 to deliver therapy according to second phase 168. In some examples, transition period 170 may be a wait on the order of approximately several milliseconds (e.g. 5 milliseconds). Processing module 132 may then control switching circuit 154 to deliver therapy according to second phase 168.

Figure 7:
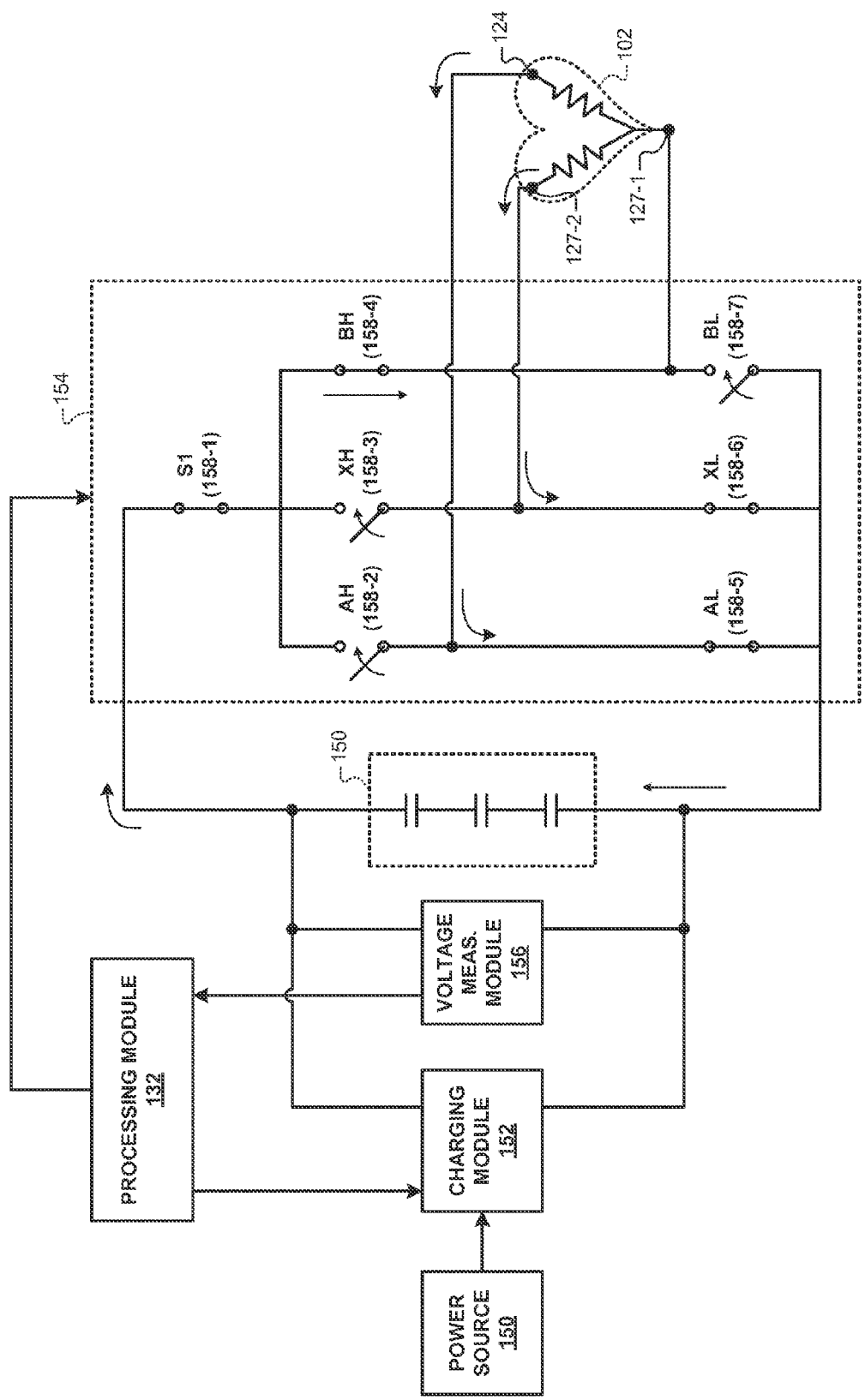
FIG. 7 is a schematic that illustrates an example switching configuration of a switching circuit that may be used to deliver a second phase of high-energy therapy.

FIG. 7 is a schematic that illustrates delivery of high-energy therapy during second phase 168. During second phase 168, processing module 132 controls switching circuit 154 to deliver energy to heart 102 in a polarity that is opposite to that delivered during first phase 166. The direction of current through switching circuit 154 and heart 102 is illustrated by arrows. In order to deliver therapy during second delivery phase 168, processing module 132 instructs switches S1 158-1, BH 158-4, AL 158-5, and XL 158-6 to close.

Voltage measuring module 156 measures the voltage across high-voltage capacitors 150 during second delivery phase 168.

Referring back to FIG. 5, the voltage waveform during second phase 168 is illustrated as negative to indicate that energy is being delivered to heart 102 from high-voltage capacitors 150 in a polarity that is opposite to that delivered during first phase 166. At the start of second phase 168 of high-energy therapy, the voltage across high-voltage capacitors 150 is approximately equal to the voltage across high-voltage capacitors 150 at the end of first phase 166. For example, the voltage across high-voltage capacitors 150 at the start of second phase is illustrated as $-V_{T1}$ in FIG. 5, which is equal in magnitude to the voltage $V_{T1}$ at the end of first phase 166.

Voltage measuring module 156 measures the voltage across high-voltage capacitors 150 during second phase 168. Voltage across high-voltage capacitors 150 may decrease during second phase 168. Processing module 132 may monitor the decrease in voltage during second phase 168. Processing module 132 may control switching circuit 154 to discontinue second phase 168 when the voltage across high-voltage capacitors 150 drops to a threshold voltage that indicates that the programmed amount of energy has been delivered during second phase 168. The threshold voltage that indicates that the programmed amount of energy has been delivered is illustrated as $-V_{T2}$.

Processing module 132 may control switching circuit 154 to discontinue delivery of high-energy therapy when processing module 132 determines that the voltage across high-voltage capacitors 150 has dropped to the threshold voltage $-V_{T2}$ (e.g., dropped to a magnitude of $V_{T2}$). In other words, processing module 132 may set the switching configuration of switching circuit 154 such that high-voltage capacitors 150 are disconnected from electrodes 124, 127 when the voltage across high-voltage capacitors 150 has dropped to $V_{T2}$. Processing module 132 may control switching circuit 154 to stop delivery of therapy during second phase 168 by instructing all switches 158 of switching circuit 154 to open. In examples where switches BH 158-4, AL 158-5, and XL 158-6 are SCR devices and switch S1 158-1 is a power MOSFET device, processing module 132 may control switch S1 158-1 to open, thereby disconnecting switches BH 158-4, AL 158-5, and XL 158-6 from high-voltage capacitors 150 and therefore setting switches BH 158-4, AL 158-5, and XL 158-6 to the open state.

Figure 9:
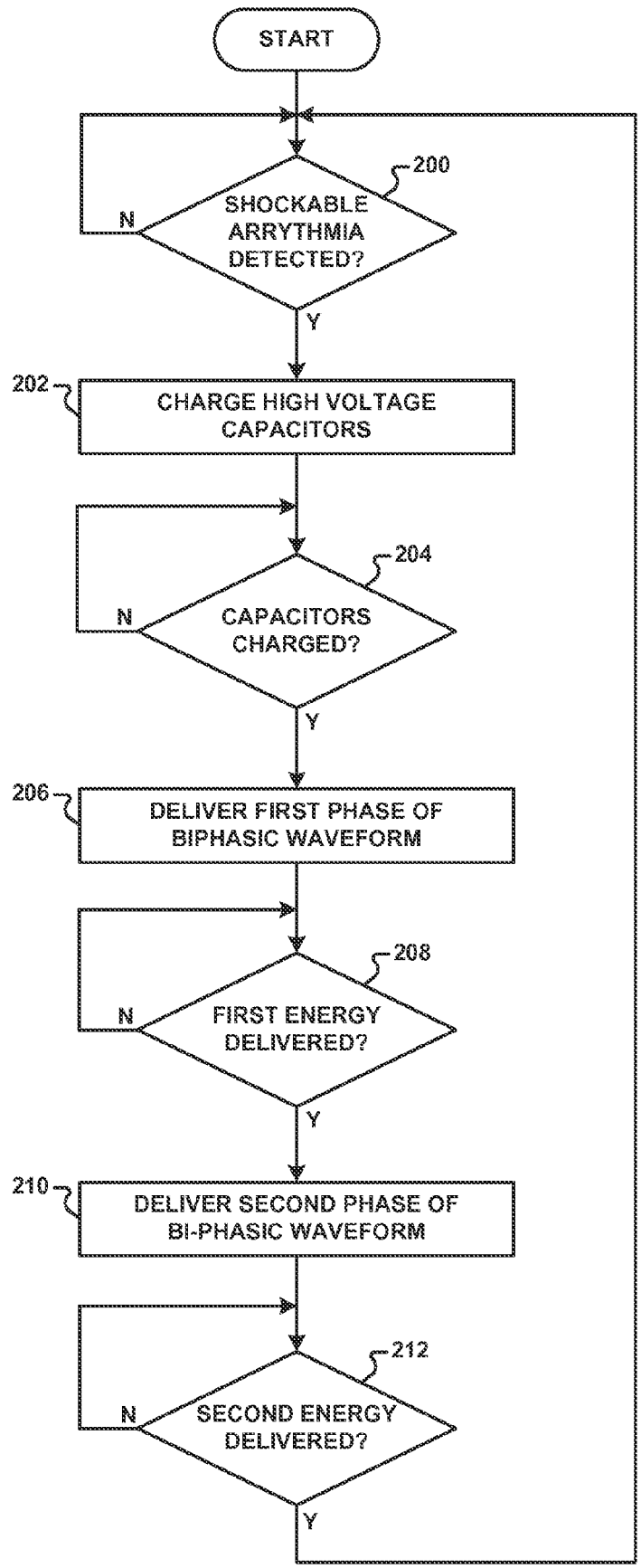
FIG. 9 is a flowchart of a method for delivering high-energy therapy using a biphasic waveform.

FIG. 9 is a flowchart of an example method for delivering high-energy therapy using a biphasic waveform. At the start of the method of FIG. 9, it may be assumed that processing module 132 is configured to deliver high-energy therapy using a biphasic waveform. The method of FIG. 9 describes a scenario where IMD 106 delivers a biphasic waveform without detecting a high impedance fault.

At the start of the method of FIG. 9, processing module 132 may be continuously monitoring heart rate to determine whether heart 102 is experiencing a shockable arrhythmia (200). If processing module 132 does not detect a shockable arrhythmia (e.g., VT/VF), processing module 132 continues monitoring heart rate. If processing module 132 detects a shockable arrhythmia, processing module 132 instructs charging module 152 to charge high-voltage capacitors 150 (202). Processing module 132 may monitor the voltage across high-voltage capacitors 150 during charging and determine whether high-voltage capacitors 150 are charged based on the magnitude of the monitored voltage (204). If processing module 132 determines that high-voltage capacitors 150 are not charged up to the charging voltage $V_0$, processing module 132 continues monitoring the voltage across high-voltage capacitors 150 until the appropriate threshold is reached.

If processing module 132 determines that high-voltage capacitors 150 are charged up to the charging voltage $V_0$, processing module 132 may disconnect charging module 152 from high-voltage capacitors 150 and control switching circuit 154 in order to deliver first phase 166 of a biphasic waveform (206). Processing module 132 may then monitor the voltage across high-voltage capacitors 150 in order to determine whether the first portion of energy has been delivered (208). If processing module 132 determines that the voltage across high-voltage capacitors 150 is greater than the first threshold voltage $V_{T1}$, processing module 132 may determine that the first portion of energy has not been delivered in block (208), and processing module 132 may continue to monitor the voltage across high-voltage capacitors 150.

If processing module 132 determines that the voltage across high-voltage capacitors 150 is less than or equal to $V_{T1}$, processing module 132 may determine that the first portion of energy has been delivered in block (208). Processing module 132 may then discontinue delivery of first phase 166 of the biphasic waveform, wait for a transition period, and then configure switching circuit 154 to deliver second phase 168 of the biphasic waveform (210).

Processing module 132 may then monitor the voltage across high-voltage capacitors 150 in order to determine whether the second portion of energy has been delivered (212). If processing module 132 determines that the voltage across high-voltage capacitors 150 is greater than the second threshold voltage $V_{T2}$, processing module 132 may determine that the second portion of energy has not been delivered in block (212), and processing module 132 may continue to monitor the voltage across high-voltage capacitors 150.

If processing module 132 determines that the voltage across high-voltage capacitors 150 is less than or equal to $V_{T2}$, processing module 132 may determine that the second portion of energy has been delivered in block (212). Processing module 132 may then discontinue delivery of second phase 168 of the biphasic waveform and return to monitoring the heart rate and determining whether a shockable arrhythmia is detected (200).

IMD 106 of the present disclosure may detect potential faults in components of IMD 106. For example, as described hereinafter, processing module 132 may detect potential faults based on information acquired during delivery of high-energy therapy. The potential faults may be manifested as high impedance faults in the electrical pathway from high-voltage capacitors 150 to electrodes 124, 127. When components of IMD 106 are functional, i.e., do not include high impedance faults, the electrical pathway from high-voltage capacitors 150 to electrodes 124, 127 is typically a low impedance path during delivery of high-energy therapy to heart 102, e.g., approximately a short circuit path. However, when the electrical pathway from high-voltage capacitors 150 to electrodes 124, 127 includes a high impedance fault, the impedance of the electrical pathway may increase from the typically low impedance value to a higher impedance value. In other words, when the electrical pathway from high-voltage capacitors 150 to electrodes 124, 127 includes a high impedance fault, the impedance of the electrical pathway may deviate from the typical short circuit impedance towards a higher impedance value, which, in some examples, may approach an open circuit impedance value. An increase in impedance in the electrical path between high-voltage capacitors 150 and electrodes 124, 127 may impede the delivery of energy to heart 102 and may therefore adversely affect the efficacy of the high-energy therapy.

The electrical path from high-voltage capacitors 150 to electrodes 124, 127 during delivery of high-energy therapy may include a variety of components. For example, as illustrated, the electrical path may include some of switches 158, conductors in lead 114, and electrodes 124, 127. Additionally, the electrical path may include electrical connections within IMD 106 that connect high-voltage capacitors 150 to switches 158, the electrical connections that form interconnects between switches 158, and the electrical connections that connect conductors of lead 114 to electrical switches 158. The electrical interconnects between high-voltage capacitors 150 and switches 158 may include metallic traces on printed circuit boards (PCBs) that provide support for electrical components within IMD 106 and metallic wires that may be used to connect conductors in lead 114 to the PCB of IMD 106.

As described above, switches 158 typically have low impedance values when operating in the closed state. For example, switches 158 may be approximated as short circuits e.g., as compared to the impedance of heart 102 as seen between electrodes 124, 127. A high impedance fault in switches 158 may cause an increase in the impedance of switches 158 when switches 158 are supposed to be operating in the closed state. For example, when switches 158 are MOSFETs, a high impedance fault may include a fault that presents an increased impedance from drain to source of the MOSFET when the MOSFET is intended to operate as a closed switch.

Typically, when lead 114 is functional, lead 114 includes continuous conductors that extend from connector block 110 to electrodes 127. Conductors within lead 114 may typically provide a low impedance path for current, e.g., approximately a short circuit. However, a high impedance fault in conductors of lead 114 may present an increased impedance in the conductors. Such a high impedance fault in the conductors of lead 114 may be caused, for example, by a fracture of the conductors of lead 114. A fracture in conductors of lead 114 may cause either an intermittent or continuously high impedance in some examples.

Typically, interconnections between electronic components of IMD 106 provide a low impedance path for current. Interconnections, as used herein, may generally describe the conductive paths between components of IMD 106. For example, interconnects may include the conductive traces (e.g., on a PCB) and wires that connect high-voltage capacitors 150 to switches 158. Additionally, interconnects may also include the conductive traces and wires that connect switches 158 to conductors of lead 114. In some examples, high impedance faults may be present in interconnects that may cause an increase in the impedance of the interconnects. For example, high impedance faults may be caused by worn or broken interconnects.

Additionally, interconnects may include the electrical connections between connector block 110 and conductors of lead 114. As described above, leads 112, 114, 116 may be mechanically connected to connector block 110. When leads 112, 114, 116 are mechanically connected, conductors of leads 112, 114, 116 may be seated against conductive contacts within connector block 110 such that conductors of leads 112, 114, 116 are electrically connected to electrical components (e.g., switches 158) within IMD 106. In some examples, high impedance faults may be present in the electrical connection between the conductors of lead 114 and the electrical contacts of connector block 110 that may cause an increase in impedance between the contacts of connector block 110 and the conductors of lead 114. For example, high impedance faults may be caused by unreliable contact between the conductors of lead 114 and the electrical contacts of connector block 110, e.g., due to shifting of lead 114 within connector block 110 caused, for example, by insufficient mechanical stabilization or incomplete insertion of the proximal ends of the leads into the connector block.

Figure 10:
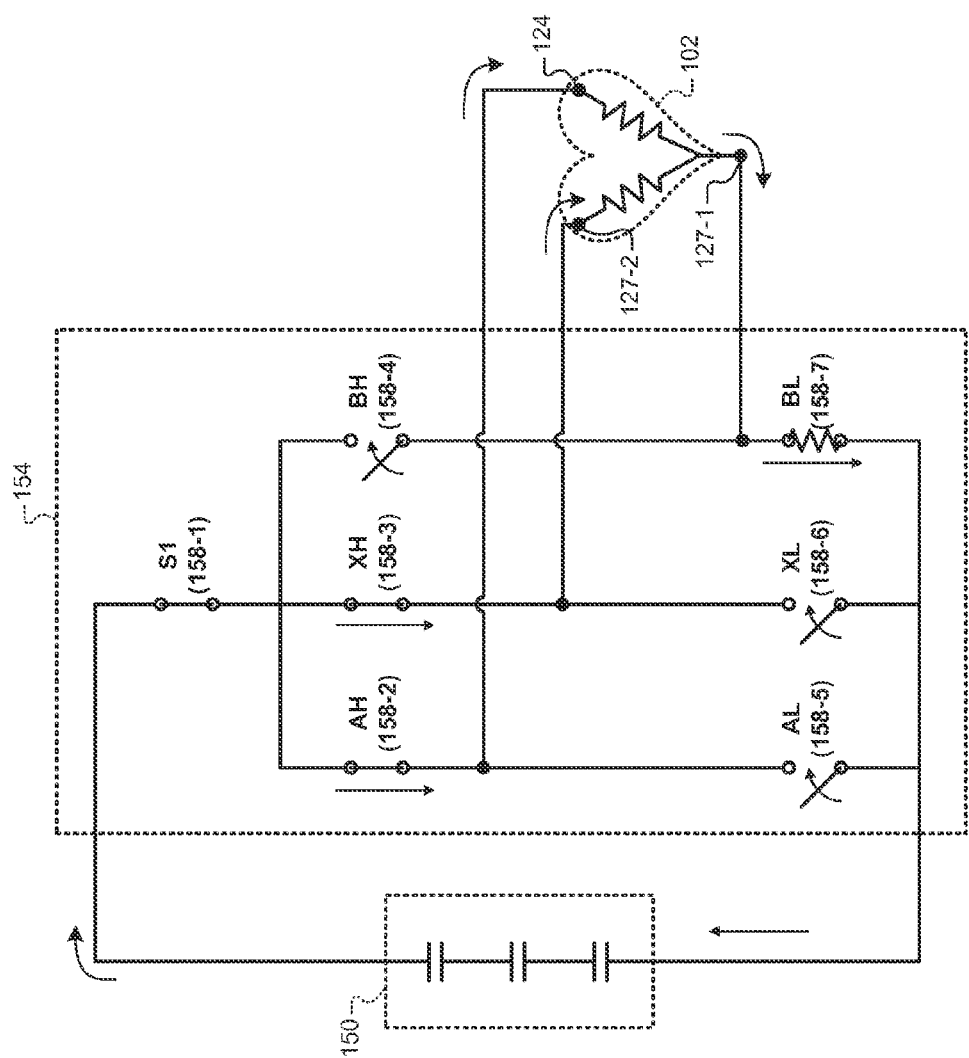
FIG. 10 is a schematic that illustrates example high impedance faults that may be present during a first phase of delivery of high-energy therapy.
Figure 12:
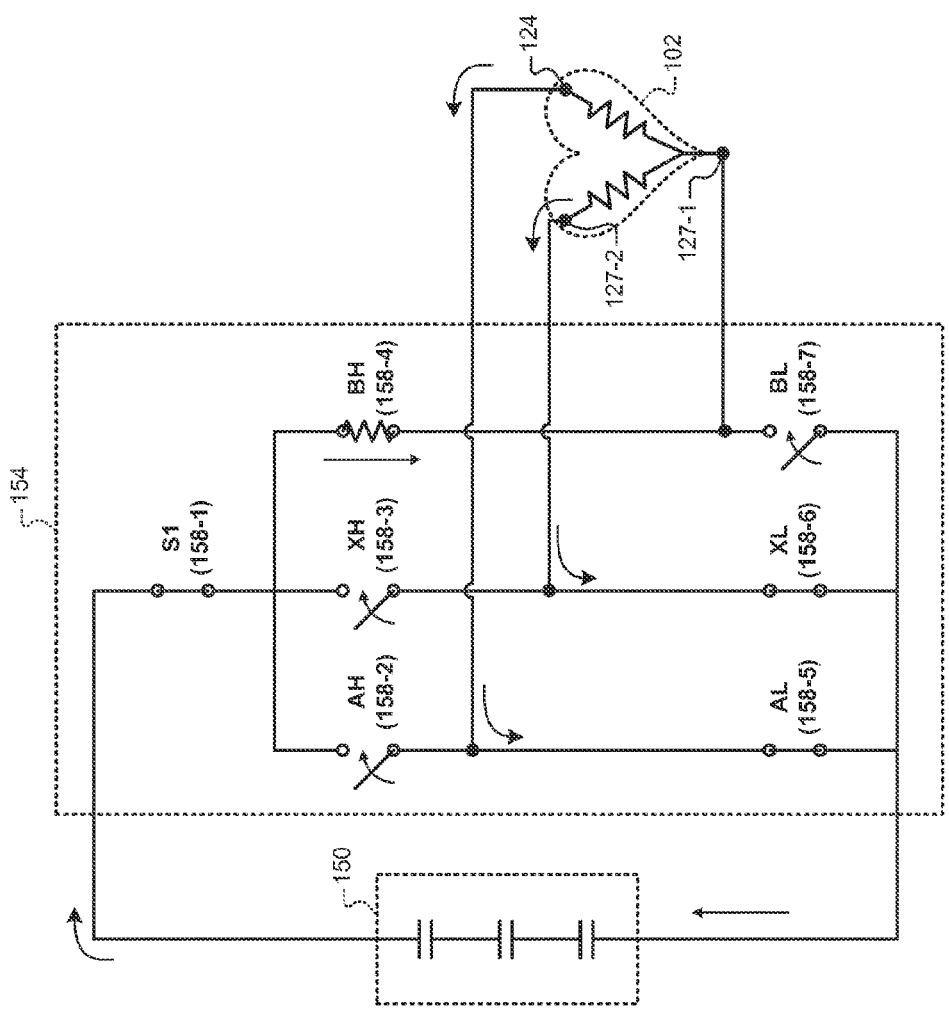
FIG. 12 is a schematic that illustrates example high impedance faults that may be present during a second phase of delivery of high-energy therapy.

FIG. 10 and FIG. 12 are schematics that illustrate example high impedance faults that may be present during delivery of high-energy therapy. FIG. 10 and FIG. 12 show high impedance faults during first phase 166 and second phase 168, respectively. High impedance faults are illustrated as resistors in place of closed switches. For example, with respect to FIG. 10, which illustrates a switching configuration for first phase 166, switch BL 158-7 is illustrated as a resistor instead of a short circuit. As another example, with respect to FIG. 12, which illustrates a switching configuration for second phase 168, switch BH 158-4 is illustrated as a resistor instead of a short circuit.

The resistors illustrated in FIG. 10 and FIG. 12, which are used in place of closed switches, may generally indicate a high impedance fault in any portion of the electrical pathway between high-voltage capacitors 150 and heart 102, and accordingly, the resistors may not only represent faults in switches, but also other portions of the conductive pathway including the switches. For example, the resistor in place of switch BL 158-7 in FIG. 10 may represent a high impedance fault in switch BL 158-7. Additionally, the resistor in place of switch BL 158-7 in FIG. 10 may represent a high impedance fault in at least one of switch AH 158-2, an interconnect connected between switch AH 158-2 and electrode HVA 124, and interconnects from high-voltage capacitors 150 to switch AH 158-2. Additionally, the resistor in place of switch BL 158-7 in FIG. 10 may represent a high impedance fault in at least one of switch XH 158-3, a conductor in lead 114 connected to switch XH 158-3, and interconnects from high-voltage capacitors 150 to switch XH 158-3. In a similar manner, the resistor across switch BH 158-4 in FIG. 12 may represent a high impedance fault in one of switches BH 158-4, AL 158-5, XL 158-6, and/or high impedance faults in the respective electrical pathways including switches BH 158-4, AL 158-5, XL 158-6, e.g., in the leads and interconnects.

The presence of a high impedance fault in any of the above described locations (e.g., a closed switch, a conductor in a lead, and/or an interconnect) may delay delivery of high-energy therapy to heart 102. In other words, the presence of a high impedance fault in the delivery path may decrease the rate at which high-voltage capacitors 150 discharge energy to heart 102. The decrease in the rate at which energy is delivered to heart 102 may adversely affect the efficacy of the high-energy therapy.

Figure 11:
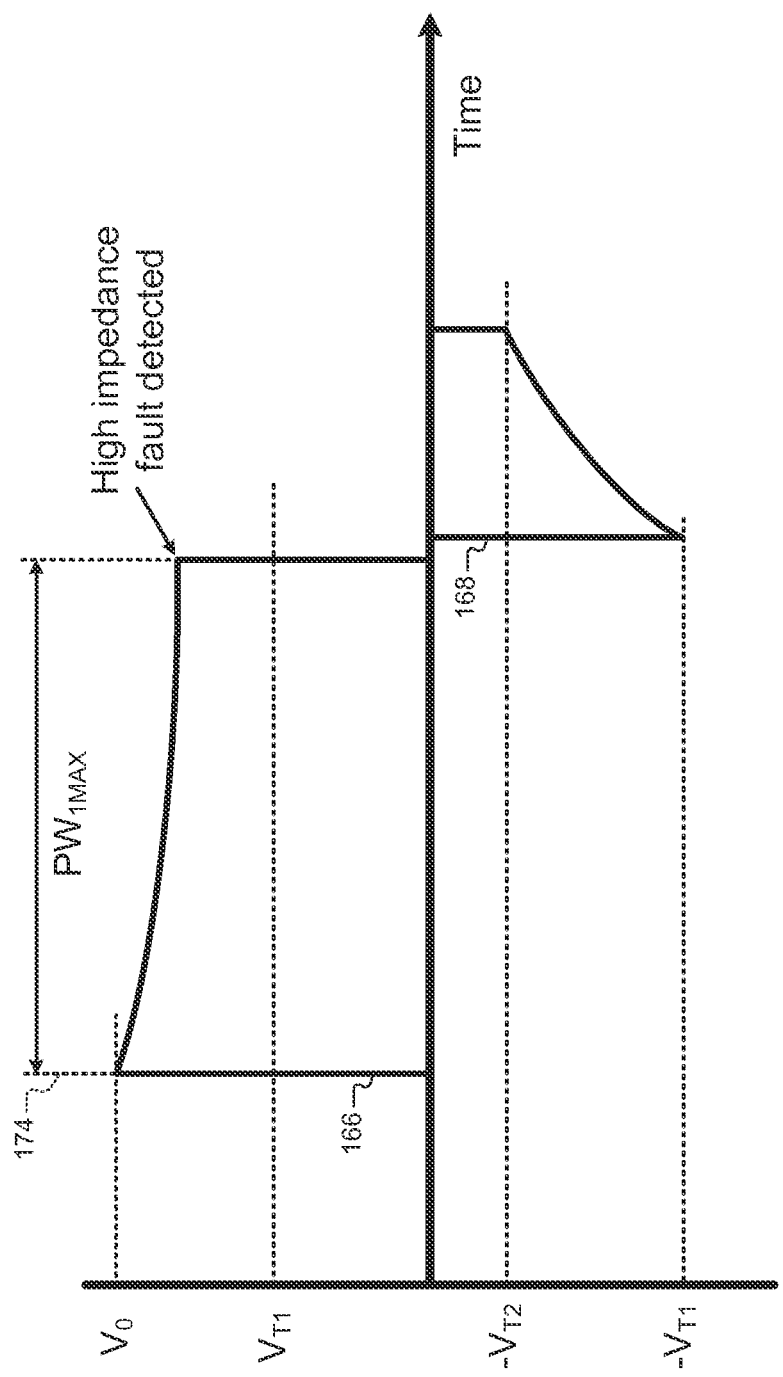
FIG. 11 shows an example biphasic waveform in which a high impedance fault is present during the first phase of delivery of high-energy therapy.

FIG. 10 and FIG. 11 show an example schematic and waveform, respectively, in which a high impedance fault is present in a delivery pathway during first phase 166. The presence of the high impedance fault may increase the amount of time required for discharge of high-voltage capacitors 150 from $V_0$ to $V_{T1}$ (i.e., $PW_1$). Similarly, with respect to the example schematic and waveform of FIG. 12 and FIG. 13, respectively, in examples where a high impedance fault is present in a delivery pathway during second delivery phase 168, the duration of time required for discharge of high-voltage capacitors 150 from $V_{T1}$ to $V_{T2}$ (i.e., $PW_2$) may increase.

Detection of a high impedance pathway during first phase 166 is described with respect to FIGS. 10-11. Detection of a high impedance pathway during second phase 168 is described with respect to FIGS. 12-13. As described above, processing module 132 may monitor the voltage across high-voltage capacitors 150 during first phase 166 to determine whether the programmed amount of energy has been delivered to heart 102. In order to detect a high impedance fault, processing module 132 may monitor the voltage across high-voltage capacitors 150 to determine whether the programmed amount of energy has been delivered to heart 102 within a predetermined amount of time. The predetermined amount of time may be referred to herein as "$PW_{1MAX}$." Processing module 132 may detect a high impedance fault during first phase 166 when processing module 132 determines that the amount of time that has elapsed during delivery of first phase 166 is greater than $PW_{1MAX}$.

The amount of time that elapses during first phase 166 may be related to an amount of impedance in the delivery pathway between high-voltage capacitors 150 and heart 102. When no fault is present in the delivery pathway during first phase 166, the impedance of switches AH 158-2, XH 158-3, and BL 158-7, conductors in lead 114, and interconnects may be relatively low, e.g., near a short circuit impedance value. Thus the impedance, as seen by high-voltage capacitors 150 during first phase 166 may be due mostly to the impedance between electrodes 124, 127, i.e., impedance of patient 104 including heart 102. When no fault is present in the delivery path during first phase 166, the amount of time that elapses during first delivery phase 166 may be at a minimum in some examples.

The presence of any high impedance faults in the delivery path during first phase 166 may tend to increase the length of first phase 166. For example, the presence of any high impedance faults in the delivery path during first phase 166 may tend to increase the duration of first phase 166 to a value that is greater than when a high impedance fault is not present in the delivery pathway. The value $PW_{1MAX}$ may be a threshold value used by processing module 132 to determine whether a high impedance fault is present in the delivery path. $PW_{1MAX}$ max may be a value that is selected such that a length of first phase 166 that is less than $PW_{1MAX}$ does not indicate a high impedance fault, while a length of first phase 166 that is greater than $PW_{1MAX}$ indicates a high impedance fault in the delivery path. In some examples, the value $PW_{1MAX}$ may be selected based on electrode placement, patient health, lead design, expected impedance, etc. In some examples, the system may also look at the voltage Vcap when $PW_{1MAX}$ is reached in order to determine the strength of the fault, e.g., a strong fault may be indicated if Vcap is approximately equal to $V_0$, while a weak fault may be indicated if Vcap is near $V_{T1}$.

With respect to FIG. 11, so long as the length of first phase 166 is less than $PW_{1MAX}$, processing module 132 may not detect a high impedance fault. However, if processing module 132 determines that the length of first phase 166 is equal to or greater than $PW_{1MAX}$, processing module 132 may detect a high impedance fault in the delivery path. FIG. 11 illustrates an example where the duration of first phase 166 reaches the value of $PW_{1MAX}$ before the voltage across high-voltage capacitors 150 drops to a value of $V_{T1}$. According to FIG. 11, first phase 166 starts at 174 with the voltage across high-voltage capacitors 150 equal to $V_0$. During first phase 166, the voltage across high-voltage capacitors 150 drops in value. However, the drop in voltage across high-voltage capacitors 150 occurs at a lesser rate in FIG. 11 than in FIG. 5, where a high impedance fault was not present, indicating that the delivery path for first phase 166 may include a high impedance fault.

Processing module 132 may transition switching circuit 154 to second phase 168 if the voltage across high-voltage capacitors 150 drops to a value of $V_{T1}$ before an amount of time $PW_{1MAX}$ has passed. If processing module 132 determines that the voltage across high-voltage capacitors 150 has not dropped to a value of $V_{T1}$ within the period of time $PW_{1MAX}$, then processing module 132 may detect a high impedance fault and then transition to second delivery phase 168.

Processing module 132 may detect high impedance faults during second phase 168 in a similar manner as processing module 132 detects high impedance faults during first phase 166. With respect to FIG. 12, the presence of any high impedance faults in the delivery path during second phase 168 may tend to increase the length of second phase 168. For example, the presence of any high impedance faults in the delivery path during second phase 168 may tend to increase the length of second phase 168 to a value that is greater than when a high impedance fault is not present in the delivery pathway. The value $PW_{2MAX}$ may be a threshold value used by processing module 132 to determine whether a high impedance fault is present in the delivery path during second phase 168. $PW_{2MAX}$ max may be a value that is selected such that a length of second phase 168 that is less than $PW_{2MAX}$ does not indicate a high impedance fault, while a length of second phase 168 that is greater than $PW_{2MAX}$ indicates a high impedance fault in the delivery path. In some examples, the value $PW_{2MAX}$ may be selected based on electrode placement, patient health, lead design, expected impedance, etc. In some examples, the system may also look at the voltage Vcap when $PW_{2MAX}$ is reached in order to determine the strength of the fault, e.g., a strong fault may be indicated if Vcap is approximately equal to $V_{T1}$, while a weak fault may be indicated if Vcap is near $V_{T2}$.

Figure 13:
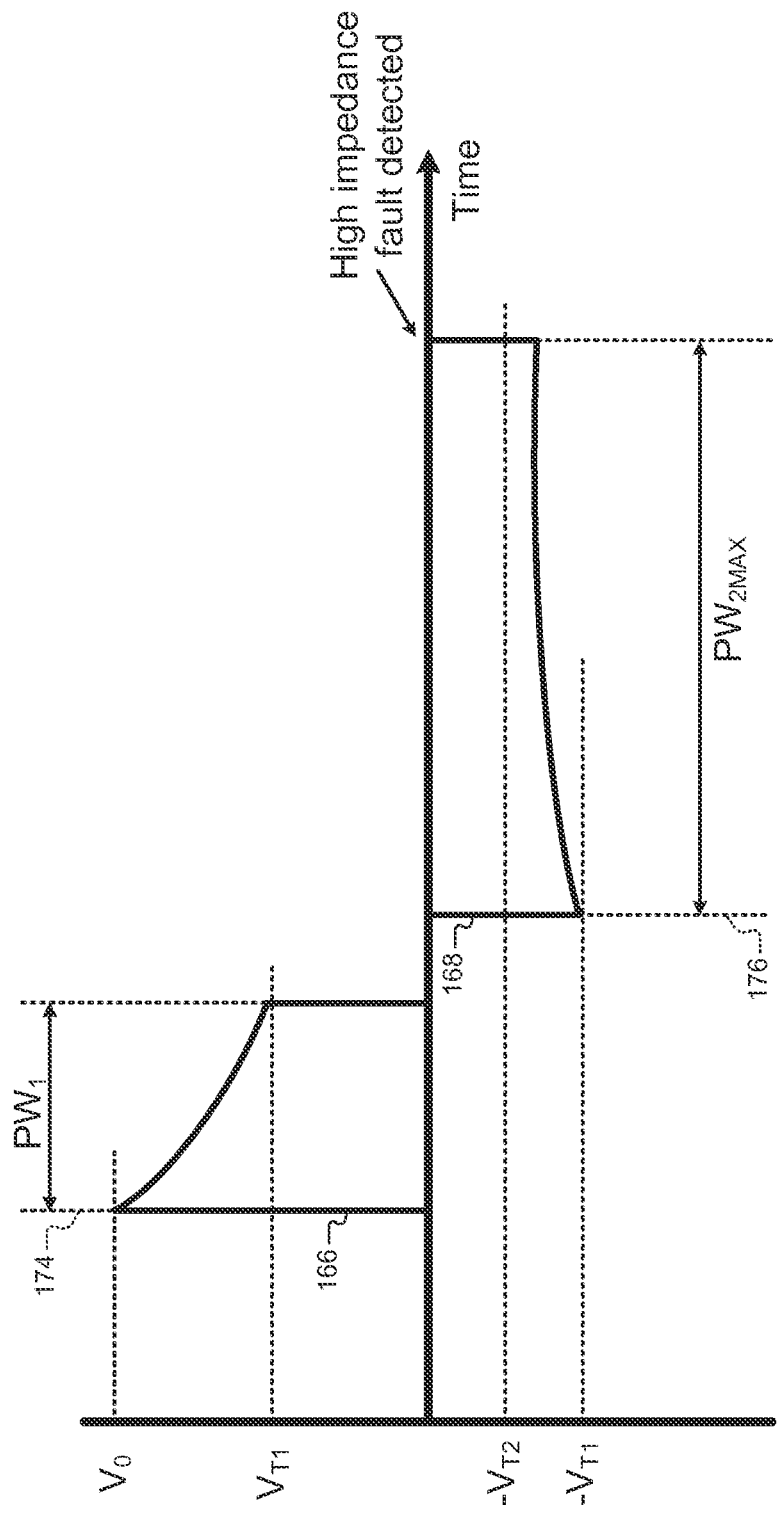
FIG. 13 shows an example biphasic waveform in which a high impedance fault is present during the second phase of delivery of high-energy therapy.

With respect to FIG. 13, so long as the length of second phase 168 is less than $PW_{2MAX}$, processing module 132 may not detect a high impedance fault. However, if processing module 132 determines that the length of second phase 168 is equal to or greater than $PW_{2MAX}$, processing module 132 may detect a high impedance fault in the delivery path. FIG. 13 illustrates an example where the duration of second phase 168 reaches the value of $PW_{2MAX}$ before the voltage across high-voltage capacitors 150 drops to a value of $V_{T2}$. According to FIG. 13, second phase 168 starts at 176 with the voltage across high-voltage capacitors 150 equal to $V_{T1}$. During second phase 168, the voltage across high-voltage capacitors 150 drops in value. However, the drop in voltage across high-voltage capacitors 150 occurs at a lesser rate in FIG. 13 than in FIG. 5, where a high impedance fault was not present, indicating that the delivery path for second phase 168 may include a high impedance fault.

Processing module 132 may stop second phase 168 if the voltage across high-voltage capacitors 150 drops to a value of $V_{T2}$ before an amount of time $PW_{2MAX}$ has passed. If processing module 132 determines that the voltage across high-voltage capacitors 150 has not dropped to a value of $V_{T2}$ within a period of time $PW_{2MAX}$, then processing module 132 may detect a high impedance fault and then stop second phase 168.

With respect to FIG. 8, processing module 132 may detect potential high impedance faults during delivery of high-energy therapy using a monophasic waveform in a similar manner as processing module 132 detects potential high impedance faults during either the first or second phases 166, 168. The presence of any high impedance faults in the delivery path during monophasic delivery may tend to increase the length of monophasic pulse 172 (i.e., $PW_{1MONO}$). Processing module 132 may include a value $MONO_{MAX}$ and a threshold voltage $V_{TMONO}$ that may be used by processing module 132 to determine whether a high impedance fault is present in the delivery path during delivery of monophasic pulse 172. Processing module 132 may determine that a high impedance fault is present during delivery of monophasic pulse 172 when the voltage across high-voltage capacitors 150 does not reach the threshold voltage $V_{TMONO}$ with a time period of $MONO_{MAX}$. $MONO_{MAX}$ may be a value that is selected such that a duration of monophasic pulse 172 that is less than $MONO_{MAX}$ does not indicate a high impedance fault, while a duration of monophasic pulse 172 that is greater than $MONO_{MAX}$ indicates a high impedance fault in the delivery path. The threshold voltage $V_{TMONO}$ may be selected by processing module 132 based on the total amount of energy to be delivered during delivery of the monophasic waveform.

Although processing module 132 may detect a high impedance fault during delivery of high-energy therapy based on the voltage measured across high-voltage capacitors 150, in other examples, processing module 132 may detect high impedance faults by monitoring the amount of current being delivered by high-voltage capacitors 150 during delivery of high-energy therapy. For example, processing module 132 may detect a high impedance fault if the amount of current being delivered during high-energy therapy is small enough to indicate that a high impedance fault is present in the conductive pathway. In these examples, a current monitoring circuit may be placed in IMD 106 that measures the amount of current delivered from high-voltage capacitors 150 during delivery of high-energy therapy and indicates the amount of current to processing module 132 so that processing module 132 may detect the high impedance fault.

Referring now to FIG. 14, a flowchart illustrates a method for detecting high impedance faults during delivery of high-energy therapy using a biphasic waveform. It may be assumed that processing module 132 is configured to deliver high-energy therapy using a biphasic waveform, as illustrated in FIG. 5.

Processing module 132 may continuously monitor the heart rate of patient 104 and determine whether heart 102 is experiencing an arrhythmia (300). If processing module 132 does not detect a shockable arrhythmia, processing module 132 continues to monitoring heart rate. If processing module 132 detects a shockable arrhythmia, processing module 132 instructs charging module 152 to charge high-voltage capacitors 150 to voltage $V_0$ (302).

Processing module 132 then instructs switching circuit 154 to deliver first phase 166 of a biphasic waveform (304). Processing module 132 may then monitor the voltage across high-voltage capacitors 150 during first phase 166 (306). During first phase 166, processing module 132 may determine whether the duration of first phase 166 is greater than $PW_{1MAX}$ (308). If the duration of first phase 166 is greater than $PW_{1MAX}$, then processing module 132 may detect a high impedance fault (310) and transition to delivering second phase 168 (312). If the duration of first phase 166 is not greater than $PW_{1MAX}$, then processing module 132 may determine whether the first portion of energy is delivered (314). If the first portion of energy has not been delivered (i.e., $Vcap > V_{T1}$), then processing module 132 continues monitoring the duration of first phase 166 in block (308). If processing module 132 determines that the first portion of energy has been delivered (i.e., $Vcap \leq V_{T1}$) then processing module 132 may discontinue delivery of first phase 166 of the biphasic waveform, wait for a transition period, and then configure switching circuit 154 to deliver second phase 168 of the biphasic waveform (312).

Processing module 132 may then monitor the voltage across high-voltage capacitors 150 during second phase 168 (314). Processing module 132 may determine whether the duration of second phase 168 is greater than $PW_{2MAX}$ (316). If the duration of second phase 168 is greater than $PW_{2MAX}$, then processing module 132 may detect a high impedance fault (318) and end high-energy therapy delivery (320). If the duration of second phase 168 is not greater than $PW_{2MAX}$, then processing module 132 may determine whether the second portion of energy is delivered (322). If the second portion of energy has not been delivered (i.e., $Vcap > V_{T2}$), then processing module 132 continues monitoring the duration of second phase 168 in block (316). If processing module 132 determines that the second portion of energy has been delivered (i.e., $Vcap \leq V_{T2}$) then processing module 132 may discontinue delivery of the high-energy therapy (320).

With respect to FIG. 3, as described above, memory 134 may include initial therapy configurations 160 and high impedance therapy configurations 162. Initially, before detection of a high impedance fault, processing module 132 may control the delivery of high-energy therapy using initial therapy configurations 160. For example, initial therapy configurations 160 may define a pattern of therapy configurations to be used by processing module 132 in scenarios where processing module 132 has not previously detected a high impedance fault during delivery of high-energy therapy.

Processing module 132 may control delivery of high-energy therapy according to initial therapy configurations 160 until a high impedance fault is detected during delivery of high-energy therapy, as described above. Upon detection of a high impedance fault during delivery of high-energy therapy, processing module 132 may begin delivering high-energy therapy according to high impedance therapy configurations 162 stored in memory 134. High impedance configurations 162 may represent N different therapy configurations 164. Each of the N therapy configurations 164 may define an electrode vector (e.g., AX>B, A>X, etc.), a waveform (e.g., biphasic/monophasic), and transition data. The transition data included in each of the N therapy configurations 164 may define a subsequent one of the N therapy configurations to select in response to detection of a high impedance fault at the current therapy selection. For example, the transition data may specify a subsequent one of the N therapy configurations to select based on when (e.g., during which phase of delivery) a high impedance fault was detected during delivery of high-energy therapy according to the current one of the N therapy configurations.

FIG. 15 shows a method for reconfiguring high-energy therapy based on detection of a high impedance fault during previous deliveries of high-energy therapy. At the start of the method of FIG. 15, it may be assumed that processing module 132 has not yet detected a high impedance fault during delivery of high-energy therapy. Accordingly, at the start of the method of FIG. 15, processing module 132 may select an initial therapy configuration (e.g., an initial electrode vector and waveform) for delivery of high-energy therapy from initial therapy configurations 160 (400). It may be assumed that the initial therapy configuration specifies that the waveform to be delivered during high-energy therapy is a biphasic waveform.

Processing module 132 may continuously monitor heart rate and determine whether heart 102 is experiencing a shockable arrhythmia (402). If processing module 132 does not detect a shockable arrhythmia, processing module 132 continues to monitoring heart rate. If processing module 132 detects a shockable arrhythmia, processing module 132 instructs charging module 152 to charge high-voltage capacitors 150 and controls switching circuit 154 in order to deliver first phase 166 of a biphasic waveform (404). Processing module 132 may monitor the voltage across high-voltage capacitors 150 during first phase 166.

Processing module 132 may determine whether a high impedance fault is present during first phase 166 (406). In examples where a high impedance fault is present during first phase 166, processing module 132 may detect the high impedance fault (408) and proceed to deliver second phase 168 of the biphasic waveform (410). In other examples, when processing module 132 does not detect a high impedance fault, processing module 132 may instruct switching circuit 154 to begin delivery of second phase 168 of the biphasic waveform after the first portion of energy is delivered. In some examples, processing module 132 may jump to block (418) upon detection of a fault in block 408.

Processing module 132 may monitor the voltage across high-voltage capacitors 150 during second phase 168 to determine whether a high impedance fault is present during second phase 168 (412). In examples where a high impedance fault is present during second phase 168, processing module 132 may detect the high impedance fault (414). In other examples, when processing module 132 does not detect a high impedance fault, processing module 132 may instruct switching circuit 154 to stop delivery of second phase 168 of the biphasic waveform after the second portion of energy is delivered.

Processing module 132 may then determine whether a fault was detected during either the first or second phases 166, 168 of the biphasic waveform (416), e.g., in either block (408) or block (414). If processing module 132 did not detect a fault during delivery of the biphasic waveform, processing module 132 may continue monitoring the heart rate in order to detect shockable arrhythmias in block (402). If processing module 132 detected a high impedance fault during delivery of the biphasic waveform in either of blocks (408) or (414), processing module 132 may select a new therapy configuration to use during a subsequent delivery of high-energy therapy (418). In other words, processing module 132 may select a new therapy configuration (i.e., a new electrode vector and/or waveform) other than the initial configuration selected in block (400) and used to deliver the high-energy therapy during which the high impedance fault was detected in either block (408) or block (414). Processing module 132 may select the new therapy configuration from high impedance therapy configurations 162. For example, processing module 132 may identify the initial therapy configuration of block (400) in high impedance therapy configurations 162, then select the new therapy configuration based on the transition data associated with the initial therapy configuration of block (400). The transition data may indicate two different new therapy configurations for selection in block (418), e.g., a first new therapy configuration that should be selected if the high impedance fault was detected during first phase 166 at block (408), or a second new therapy configuration that should be selected if the high impedance fault was detected during second phase 168 at block (414). Processing module 132 may select one of the first and second new therapy configurations in block (418) based on when the fault was detected, e.g., based on the phase in which the fault was detected.

The first and second new therapy configurations, which may be selected in block (418), may be included in high impedance therapy configurations 162, and each of the first and second therapy configurations may also include transition data that indicates future selections for therapy configurations based on when faults are detected in the first and second therapy configurations. FIGS. 17-18 include state diagrams that illustrate possible, but not exhaustive, therapy configurations and selections of new therapy configurations based on when faults are detected.

With respect to FIG. 15, processing module 132 may then continue monitoring heart rate in order to determine whether a shockable arrhythmia is present (402). If a shockable arrhythmia is detected, processing module 132 may deliver high-energy therapy using the selected new therapy configuration, i.e., the new electrode vector and/or waveform selected in block (418).

FIG. 16 shows a method for selecting new therapy configurations in response to detection of high impedance faults. At the start of the method of FIG. 16, it may be assumed that processing module 132 is monitoring the heart rate of patient 104. Initially, processing module 132 is configured to deliver high-energy therapy according to an initial therapy configuration specified in initial therapy configurations 160 (500). The initial therapy configuration may specify an initial electrode vector and an initial waveform (e.g., either monophasic or biphasic).

Processing module 132 may monitor the heart rate of patient 104 to determine whether heart 102 is experiencing a shockable arrhythmia (502). If processing module 132 does not detect a shockable arrhythmia, processing module 132 continues to monitor the heart rate. If processing module 132 detects a shockable arrhythmia, processing module 132 instructs charging module 152 to charge high-voltage capacitors 150 and controls switching circuit 154 to deliver high-energy therapy according to the initial therapy configurations 160 (504), e.g., using the initial electrode vector and the initial waveform selected in block (500).

Processing module 132 may monitor the voltage across high-voltage capacitors 150 during delivery of high-energy therapy according to the initial therapy configuration. Processing module 132 may determine whether a high impedance fault was present during delivery of high-energy therapy (506). If processing module 132 does not detect a high impedance fault, processing module 132 may continue to monitor the heart rate of patient 104 to determine whether a shockable arrhythmia is present in block (502).

If processing module 132 detected a high impedance fault during delivery of high energy therapy in block (504), processing module 132 may proceed to select a new delivery configuration from high impedance therapy configurations 162. As described above, high impedance therapy configurations 162 may specify N therapy configurations 164 that processing module 132 may use to deliver high-energy therapy. Each of N therapy configurations 164 may specify an electrode vector used for delivery of the high-energy therapy. Each of N delivery configurations 164 may also specify the type of waveform used for delivery of high-energy therapy. Each of N therapy configurations 164 may also include transitional data that specifies a subsequent therapy configuration of the N delivery configurations 164 that processing module 132 is to select in the event that a high impedance fault is detected during delivery using the current therapy configuration. When a current therapy configuration specifies that a biphasic waveform is to be delivered, the transitional data associated with that current therapy configuration may specify that processing module 132 is to select a first therapy configuration of the N therapy configurations 164 if a fault is detected during first phase 166, and that processing module 132 is to select a second therapy configuration of the N therapy configurations 164 if a fault is detected during second phase 168.

With respect to block (508), after a fault was detected during delivery of therapy according to the initial therapy configuration, processing module 132 may identify the initial therapy configuration in high impedance configurations 162 (508), then processing module 132 may select a new therapy configuration from high impedance configurations 162 based on when the fault was detected during delivery according to the initial therapy configuration (510). For example, processing module 132 may select the new therapy configuration from high impedance configurations 162 based on which phase of the biphasic waveform presented the high impedance fault. The new therapy configuration to be selected may be specified by transitional data associated with the initial therapy configuration.

Processing module 132 may then monitor the heart rate of patient 104 to determine whether patient 104 is experiencing a shockable arrhythmia (512). If processing module 132 does not detect a shockable arrhythmia, processing module 132 continues to monitor the heart rate (512). If processing module 132 detects a shockable arrhythmia, processing module 132 instructs charging module 152 to charge high-voltage capacitors 150 and controls switching circuit 154 to deliver high-energy therapy according to the new therapy configuration selected in block (510) from high impedance configurations 162 (514).

Processing module 132 may monitor the voltage across high-voltage capacitors 154 during delivery of high-energy therapy according to the new therapy configuration. Processing module 132 may determine whether a high impedance fault was present during delivery of high-energy therapy (516). If processing module 132 does not detect a high impedance fault, processing module 132 may continue to monitor the heart rate of patient 104 to determine whether a shockable arrhythmia is present in block (512).

If processing module 132 detected a high impedance fault during delivery of high energy therapy in block (514), processing module 132 may proceed to select another new delivery configuration from high impedance therapy configurations 162 in block (508). For example, processing module 132 may select the next therapy configuration based on the current therapy configuration and based on when the fault was detected in block (514). Processing module 132 may select the next therapy configuration according to transition data associated with the current therapy configuration, as described above.

According to the method of FIG. 16, processing module 132 may continue to update the therapy configuration used to deliver high-energy therapy so long as high impedance faults continue to be detected during delivery of the high-energy therapy. In this manner, processing module 132 may selectively transition from one therapy configuration to another according to the pattern specified in high impedance configurations 162.

FIG. 17 shows a state diagram that graphically illustrates example high impedance therapy configurations 162 that may be selected by processing module 132. Each state of FIG. 17 indicates one of the N therapy configurations. For example, state 178-1 (i.e., configuration 178-1) represents a therapy configuration that specifies electrode vector AX>B and a biphasic waveform. As another example, state 178-2 represents a therapy configuration that specifies electrodes B>AX and a monophasic waveform. The transition conditions "PW1 Fault" and "PW2 Fault" may represent detection of a fault during first and second phases 166, 168, respectively. The transition labeled "Fault" may indicate that a fault was detected during monophasic pulse 172.

The transition "OK", that redirects back to the same state, may indicate that no fault was detected during delivery of high-energy therapy and that processing module 132 may continue using the same therapy configuration in an event that no fault is detected. The states and the transitions between the states in FIG. 17 may illustrate example data included in high impedance configurations 162. For example, a state (e.g., 178-1) may indicate a current therapy configuration in high impedance configurations 162. The transitions from the state may represent data included in transition data that indicates a subsequent therapy configuration based on when a fault was detected in the current state. State 178-1, that specifies therapy configuration AX>B and a biphasic waveform, may transition to state 178-2 or state 178-3, depending on when a fault is detected. Transition data associated with configuration 178-1 may indicate that if a fault is detected during first phase ($PW_1$) 166 of therapy configuration 178-1, processing module 132 is to select therapy configuration 178-2 for subsequent deliveries of high-energy therapies. Transition data associated with configuration 178-1 may also indicate that if a fault is detected during second phase ($PW_2$) 168 of therapy configuration 178-1, processing module 132 is to select therapy configuration 178-3 for subsequent deliveries of high energy therapies.

According to FIG. 17, high impedance therapy configurations 162 may include therapy configurations using only two electrodes and therapy configurations using three electrodes. Therapy configurations using only electrodes may use either monophasic or biphasic waveforms, and therapy configurations using three electrodes may use either monophasic or biphasic waveforms. In some examples, transition data may indicate that processing module 132 transition from a therapy configuration using three electrodes to a therapy configuration using only two electrodes. For example, if processing module 132 detects a fault during delivery of therapy according to therapy configuration 178-3, which uses three electrodes, processing module 132 may select therapy configuration 178-5, which may include only 2 electrodes.

In some examples, transition data may indicate that processing module 132 transition from a therapy configuration using a biphasic waveform to a therapy configuration using a monophasic waveform. For example, if processing module 132 detects a fault during delivery of therapy according to therapy configuration 178-1, which uses a biphasic waveform, processing module 132 may select either therapy configuration 178-2 or therapy configuration 178-3, both of which use monophasic waveforms.

As described above, processing module 132 may transition from initial therapy configurations 160 to high impedance configurations 162 upon detection of a fault. Processing module 132 may perform the transition from initial therapy configurations 160 to high impedance configurations 162 by first determining the current therapy configuration (i.e., of initial therapy configurations 160) in which a fault was detected. Second, processing module 132 may identify that current therapy configuration in high impedance configurations 162. Then processing module 132 may determine the subsequent therapy configuration based on the transition data associated with the identified therapy configuration. In terms of the state chart of FIG. 17, assuming processing module 132 controlled delivery of therapy using an initial therapy configuration of "AX>B, biphasic" from initial therapy configurations 160, and further assuming that processing module 132 detected a fault during first phase 166 using that configuration, processing module 132 would first identify therapy configuration 178-1 in high impedance configurations. Then processing module 132 would select therapy configuration 178-2 since the fault was detected during first phase 166 of the previously delivered therapy. Accordingly, processing module 132 would select a subsequent therapy configuration 178-2 (in high impedance configurations 162) in response to detecting a fault during first phase 166 of therapy configuration "AX>B, biphasic" included in initial therapy conditions 160.

The state diagram of FIG. 18 graphically illustrates example high impedance therapy configurations 162 that may be selected by processing module 132. The state diagram of FIG. 18 differs from that of FIG. 17 in that it includes different therapy configurations, e.g., electrode vectors X>B and B>X. Accordingly, the state diagram of FIG. 18 illustrates additional examples of possible therapy configurations that may be included in high impedance configurations 162. The state diagrams of FIGS. 17-18 are not exhaustive examples of all possible state diagrams, nor are the state diagrams exhaustive examples of all possible high impedance configurations 162 (i.e., electrode vectors, waveforms, transitions). It is contemplated that other high impedance configurations may be implemented according to the present disclosure, e.g., different electrode vectors, waveforms, and transitions, depending on the components included in IMD 106, the arrangement of the electrodes of IMD 106, and the types of potential faults that may occur in IMD 106.

The electrode vectors and waveforms used in high impedance therapy configurations 162 along with the transitions between high impedance therapy configurations 162 may be created based on a variety of parameters and then subsequently programmed into IMD 106. For example, high impedance therapy configurations 162 may be created based on knowledge of the components included in IMD 106, knowledge of potential faults that may occur in IMD 106 (e.g., in switches 158, conductors in leads 112, 114, 116, and interconnects), and knowledge of the probability that such potential faults may occur. In other words, high impedance configurations 162 may be hardware specific parameters that are defined based on knowledge of the hardware included in IMD 106, and knowledge of the potential problems that may be caused by particular hardware failures in the device. Creation of high impedance parameters 162 based on this knowledge of potential faults may allow for programming of improved therapy reconfiguration patterns into IMD 106. Such improved therapy reconfigurations may increase the probability of avoiding high impedance faults during subsequent therapy deliveries while simultaneously maintaining an efficacious therapy configuration for treatment of a detected arrhythmia.

FIGS. 19-20 show tables that include information that may be used to generate a pattern of therapy configurations for delivery of defibrillation therapy in response to detection of high impedance faults. In other words, the tables of FIGS. 19-20 may include information that may be used to generate high impedance configurations 162. The information included in the tables may be based on the components and operation of IMD 106 as described herein with respect to FIG. 4. In other words, the information included in FIGS. 19-20 may be based on knowledge of the layout of switches 158 and the connections between switches 158 and electrodes 124, 127 during delivery of high-energy therapy using either monophasic, biphasic, or multiphasic waveforms.

FIG. 19 shows potential delivery path impedance bottlenecks. The first column lists electrode vectors and waveforms (b=biphasic, m=monophasic) of various therapy configurations. The second column lists the possible causes of high impedance faults if a fault occurs during the first phase of a biphasic delivery or during a monophasic delivery. The third column lists the possible causes of high impedance faults if a fault occurs during the second phase of a biphasic delivery. The fourth column lists the possible causes of the high impedance faults if faults occur in both the first and second phases of the biphasic delivery. As illustrated in FIG. 19, faults detected in therapy configurations may be associated with the components of the IMD, e.g., the switches, conductors in leads, and electrodes. Based on the impedance bottleneck information included in FIG. 19, high impedance configurations may be generated that may optimally work around potential bottlenecks. For example, since a fault detected during first phase 166 using configuration AX>B(b) may imply that there are possible high impedance issues in switches AH 158-2 and XH 158-3 or BL 158-7, therapy configurations may be generated that attempt to work around such a fault by working around using switches AH 158-2, XH 158-3, and BL 158-7 if such a fault is detected. Accordingly, using the information included in FIG. 19, high impedance configurations may be generated that attempt to work around specifically identified component defects of IMD 106 that may cause high impedance faults. Such high impedance therapy configurations, which may be based on the specific hardware configuration of IMD 106, may provide a robust fault tolerant therapy selection pattern for IMD 106.

FIG. 20 shows a table that lists potential reconfiguration options for faulty components. The first column lists potentially faulty switches, e.g., switches that may be suspected in a fault based on failures that are detected during therapy deliveries listed in the second column. For example, based on row 1, if a fault occurred in therapy configuration AX>B (during the first phase of a biphasic waveform or during a monophasic waveform), switches AH 158-2 and XH 158-3 may be suspected to be faulty. Row 1, column 3 indicates that a potential bypass could be therapy configuration B>AX using a monophasic waveform. This decision is illustrated in the state diagram of FIG. 17. Accordingly, the table of FIG. 20 may convey similar information as the state diagrams.

The table of FIG. 20 (and the state diagrams) may have been constructed by taking into account two different considerations. First, the potential reconfiguration vectors may have been selected in order to attempt to avoid failures detected during prior therapy configurations. Second, although avoidance of prior failures is a concern, the potential reconfiguration vectors may also be based on the suspected efficacy of a potential reconfiguration. Accordingly, high impedance configurations 162 may be generated by selecting those therapy configurations that are most efficacious while at the same time having a high probability of working around detected faults. In some examples, the probability and efficacy determinations, and accordingly, the generation of high impedance configurations 162, may be based on clinically observed data.

In some examples, after implantation in patient 104, processing module 132 may store, in memory 134, information relating to detected faults. For example, processing module 132 may store the pattern of therapy configurations attempted in response to detected faults along with the timing of the detected faults. In some examples, the clinician may retrieve the information relating to detected faults from IMD 106 via programmer 130 and use the information to diagnose potential problems with IMD 106.

As described above, the IMD of the present disclosure may step through a variety of different therapy configurations in order to bypass one or more detected high impedance faults. Although the IMD of the present disclosure is described above as stepping through a variety of different therapy configurations in response to detection of high impedance faults, the IMD of the present disclosure may use similar techniques as described herein to step through a variety of different therapy configurations in response to detection of short circuit faults that redirect current (e.g., shunt current) away from the heart during delivery of high-energy therapy. For example, the IMD of the present disclosure may select a subsequent therapy configuration based on the parameters of the current therapy configuration (e.g., the electrode vector and waveform) and based on when the short circuit fault occurred during delivery according to the current therapy configuration (e.g., during either the first or second phase of a biphasic waveform). In this manner, the IMD of the present disclosure may step through a variety of different therapy configurations in order to bypass one or more detected short circuit faults. Example techniques for stepping through a variety of different therapy configurations in order to bypass one or more detected short circuit faults are described in U.S. patent application Ser. No. 13/221617, filed herewith, and entitled "Short Circuit Fault-Tolerance in an Implantable Medical Device", which is incorporated herein by reference in its entirety.

Various examples have been described. These and other examples are within the scope of the following claims.

What is claimed is:

1. A medical device comprising:
an energy storage device configured to store electrical energy for delivery of defibrillation therapy to a heart;
a plurality of electrodes;
a memory that stores N therapy configurations, each of the N therapy configurations defining which of the plurality of electrodes are used to deliver defibrillation therapy and further defining a waveform to be applied during delivery of defibrillation therapy, wherein N is an integer that is greater than 1;
a switching circuit configured to connect the plurality of electrodes to the energy storage device; and
a processing module configured to:
control the switching circuit to deliver defibrillation therapy according to a first therapy configuration of the N therapy configurations;
detect a fault during delivery of the defibrillation therapy according to the first therapy configuration; and
select a second therapy configuration of the N therapy configurations based on when the fault was detected during delivery of the defibrillation therapy according to the first therapy configuration.

2. The medical device of claim 1, wherein the fault is a high impedance fault present in a conductive path used during defibrillation therapy according to the first therapy configuration.

3. The medical device of claim 2, wherein the high impedance fault includes a break in the conductive path, and wherein the break presents a high impedance during defibrillation therapy.

4. The medical device of claim 2, wherein the plurality of electrodes are coupled to the switching circuit using conductors, wherein the high impedance fault includes a break in one of the conductors, and wherein the break presents a high impedance during defibrillation therapy.

5. The medical device of claim 2, wherein the high impedance fault includes a break in one of the plurality of electrodes, and wherein the break presents a high impedance during defibrillation therapy.

6. The medical device of claim 2, wherein the switching circuit includes a plurality of switches, wherein the processing module is configured to instruct one of the plurality of switches to close in order to deliver defibrillation therapy according to the first therapy configuration, and wherein the high impedance fault includes a malfunction in the one of the plurality of switches that causes the one of the plurality of switches to present a high impedance when instructed to close.

7. The medical device of claim 2, wherein the processing module is configured to detect the high impedance fault based on a rate of discharge of the energy storage device during delivery of defibrillation therapy according to the first therapy configuration.

8. The medical device of claim 1, wherein the fault is a short circuit path that shunts current away from the heart during delivery of defibrillation therapy.

9. The medical device of claim 8, wherein the processing module is configured to detect the fault based on an amount of current through the switching circuit during delivery of defibrillation therapy according to the first therapy configuration.

10. The medical device of claim 1, wherein the first therapy configuration specifies the delivery of defibrillation therapy using a biphasic waveform, and wherein the second therapy configuration specifies the delivery of defibrillation therapy using a monophasic waveform.

11. The medical device of claim 1, wherein the first therapy configuration specifies the delivery of defibrillation therapy using three electrodes, and wherein the second therapy configuration specifies the delivery of defibrillation therapy using only two electrodes.

12. The medical device of claim 1, wherein the waveform defined by each of the N therapy configurations includes one of a monophasic waveform or a biphasic waveform, wherein the biphasic waveform includes a first phase and a second phase, and wherein the processing module is configured to select the second therapy configuration based on which of the first and second phases included the fault.

13. The medical device of claim 1, wherein each of the N therapy configurations is associated with corresponding transition data that specifies one or more subsequent therapy configurations of the N therapy configurations to be selected by the processing module in the case that the processing module detects a fault.

14. The medical device of claim 13, wherein the processing module is configured to select the second therapy configuration based on the transition data associated with the first therapy configuration when the processing module detects the fault during delivery of the defibrillation therapy according to the first therapy configuration.

15. A medical device comprising:
an energy storage device configured to store electrical energy for delivery of defibrillation therapy to a heart;
a plurality of electrodes;
a switching circuit configured to connect the plurality of electrodes to the energy storage device; and
a processing module configured to:
control the switching circuit to deliver defibrillation therapy using a first set of the plurality of electrodes and using a biphasic waveform that includes first and second phases;
detect a fault during one of the first and second phases of the biphasic waveform; and
select a second set of the plurality of electrodes and one of a biphasic or monophasic waveform for delivery of a subsequent defibrillation therapy, wherein the selection is based on which one of the first and second phases of the biphasic waveform included the detected fault.

16. The medical device of claim 15, wherein the fault is a high impedance fault present in a conductive path used during defibrillation therapy.

17. The medical device of claim 16, wherein the high impedance fault includes a break in the conductive path, and wherein the break presents a high impedance during defibrillation therapy.

18. The medical device of claim 16, wherein the plurality of electrodes are coupled to the switching circuit using conductors, wherein the high impedance fault includes a break in one of the conductors, and wherein the break presents a high impedance during defibrillation therapy using the first set of the plurality of electrodes.

19. The medical device of claim 16, wherein the high impedance fault includes a break in one of the electrodes, and wherein the break presents a high impedance during defibrillation therapy using the first set of the plurality of electrodes.

20. The medical device of claim 16, wherein the switching circuit includes a plurality of switches, wherein the processing module is configured to instruct one of the plurality of switches to close in order to deliver defibrillation therapy using the first set of the plurality of electrodes, and wherein the high impedance fault includes a malfunction in the one of the plurality of switches that causes the one of the plurality of switches to present a high impedance when instructed to close.

21. The medical device of claim 15, wherein the processing module is configured to control the switching circuit to deliver defibrillation therapy according to the second set of the plurality of electrodes and the selected one of the biphasic or monophasic waveforms.

22. The medical device of claim 15, wherein the second set of the plurality of electrodes is the same as the first set of the plurality of electrodes.

23. The medical device of claim 15, wherein the first set of the plurality of electrodes includes three electrodes, and wherein the second set of the plurality of electrodes includes only two electrodes.

24. The medical device of claim 15, wherein the first set of the plurality of electrodes includes three electrodes, and wherein the second set of the plurality of electrodes includes three electrodes.

25. The medical device of claim 15, wherein the processing module is configured to select the second set of the plurality of electrodes and a monophasic waveform for delivery of the subsequent defibrillation therapy when the fault is detected, regardless of which of the first and second phases includes the fault.

26. The medical device of claim 15, wherein the fault is a short circuit path that shunts current away from the heart during delivery of defibrillation therapy.

27. A method comprising:
  storing N therapy configurations in a memory of a medical device, each of the N therapy configurations defining which of a plurality of electrodes are used to deliver defibrillation therapy and further defining a waveform to be applied during delivery of defibrillation therapy, wherein N is an integer that is greater than 1;
  controlling a switching circuit to deliver defibrillation therapy from an energy storage device according to a first therapy configuration of the N therapy configurations;
  detecting a fault during delivery of the defibrillation therapy according to the first therapy configuration; and
  selecting a second therapy configuration of the N therapy configurations based on when the fault was detected during delivery of the defibrillation therapy according to the first therapy configuration.

28. The method of claim 27, wherein the fault includes one of a high impedance fault and a short circuit fault, wherein the high impedance fault is presented as a high impedance in a conductive path used during defibrillation therapy, and wherein the short circuit fault shunts current away from the heart during delivery of defibrillation therapy.

* * * * *